US008211487B2

(12) United States Patent
Damodaran

(10) Patent No.: US 8,211,487 B2
(45) Date of Patent: Jul. 3, 2012

(54) INHIBITION OF ICE CRYSTAL GROWTH

(76) Inventor: Srinivasan Damodaran, Middleton, WI (US)

( * ) Notice: Subject to any disclaimer, the term of this patent is extended or adjusted under 35 U.S.C. 154(b) by 198 days.

(21) Appl. No.: 12/624,527

(22) Filed: Nov. 24, 2009

(65) Prior Publication Data

US 2010/0151096 A1 Jun. 17, 2010

Related U.S. Application Data

(60) Provisional application No. 61/118,241, filed on Nov. 26, 2008.

(51) Int. Cl.
*A23L 1/05* (2006.01)
*C07K 1/00* (2006.01)
*A61K 47/00* (2006.01)

(52) U.S. Cl. ........................ 426/576; 435/273; 514/774
(58) Field of Classification Search .................... None
See application file for complete search history.

(56) References Cited

U.S. PATENT DOCUMENTS

| | | | |
|---|---|---|---|
| 5,179,017 A | 1/1993 | Axel et al. |
| 5,501,979 A | 3/1996 | Geller et al. |
| 5,561,063 A | 10/1996 | Hock et al. |
| 5,604,090 A | 2/1997 | Alexander et al. |
| 5,624,820 A | 4/1997 | Cooper |
| 5,665,577 A | 9/1997 | Sodroski et al. |
| 5,674,703 A | 10/1997 | Woo et al. |
| 5,693,508 A | 12/1997 | Chang |
| 5,700,470 A | 12/1997 | Saito et al. |
| 5,719,054 A | 2/1998 | Boursnell et al. |
| 5,731,172 A | 3/1998 | Saito et al. |
| 5,786,340 A | 7/1998 | Henning et al. |
| 5,821,235 A | 10/1998 | Henning et al. |
| 5,928,944 A | 7/1999 | Seth et al. |
| 6,013,516 A | 1/2000 | Verma et al. |
| 6,110,456 A | 8/2000 | During |

FOREIGN PATENT DOCUMENTS

| | | |
|---|---|---|
| WO | WO 92/05266 A2 | 4/1992 |
| WO | WO 92/14829 A1 | 9/1992 |

OTHER PUBLICATIONS

Gore, H. C., Action of Papain on the Polarization of Gelatin, Oct. 15, 1929, Industrial and Engineering Chemistry 1(4):203-205.*
Damodaran, S., Inhibition of Ice Crystal Growth in Ice Cream Mix by Gelatin Hydrolysate, 2007, Journal of Agricultural and Food Chemistry 55:10918-10923.*
Beall, P., (1983), States of Water in Biological Systems, *Cryobiology*, vol. 20, Issue 3, pp. 324-334.
Berger et al., (1970), Mapping the active site of papain with the aid of peptide substrates and inhibitors, *Phil. Trans. Roy. Soc. Lond. B*, 257:249-264.
Bitter, (1987), Heterologous Gene Expression in Yeast, *Methods in Enzymology*, 152:673-684.
Blond, G., (1988), Velocity of Linear Crystallization of Ice in Macromolecular Systems, *Cryobiology*, vol. 25, Issue 1, pp. 61-66.
Budiaman et al., (1987), Linear Rate of Water Crystallization as Influenced by Viscosity of Hydrocolloid Suspension, *J. Dairy Sci.*, 70:547-554.
Buyong et al., (1988), Amount and Size of Ice Crystals in Frozen Samples as Influenced by Hydrocolloids, *J. Dairy Sci.*, 71:2630-2639.
Chen et al., (1999), Ice-Binding Surface of Fish Type III Antifreeze, *Biophys. J.*, 77:1602-1608.
Cone et al., (1984), High-efficiency gene transfer into mammalian cells: Generation of helper-free recombinant retrovirus with broad mammalian host range, *Proc. Natl. Acad. Sci.*, USA 81:6349.
Flores et al., (1999), Ice Crystal Size Distributions in Dynamically Frozen Model Solutions and Ice Cream as Affected by Stabilizers, *J. Dairy Sci.*, 82:1399-1407.
Gilbert et al., (2004), Demonstration of antifreeze protein activity in Antarctic lake bacteria, *Microbiology*, 150:171-180.
Goff et al., (1993), The Influence of Polysaccharides on the Glass Transition in Frozen Sucrose Solutions and Ice Cream, *J. Dairy Sci.*, 76:1268-1275.
Graether et al., (2000), B-Helix structure and ice-binding properties of hyperactive antifreeze protein from an insect, *Nature*, 406:325-328.
Graether et al., (2004), Cold Survival in freeze-intolerant insects, *Eur. J. Biochem.*, 271:3285-3296.
Graham et al., (1997), Hyperactive antifreeze protein from beetles, *Nature*, 388:727-728.
Graham et al., (2005), Glycine-Rich Antifreeze Proteins from Snow Fleas, *Science*, 310:461.
Grant et al., (1987), Expression and Secretion Vectors for Yeast, *Methods in Enzymology*, 153:516-544.
Hagiwara et al., (1996), Effect of Sweetener, Stabilizer, and Storage Temperature on Ice Recrystallization in Ice Cream, *J. Dairy Sci.*, 79:735-744.
Harper et al., (1983), Effect of Locust Bean Gum and Selected Sweetening Agents on Ice Recrystallization Rates, *J. Food Sci.*, 48:1801-1809.
Hew et al., (1992), Protein Interaction with Ice, *Eur. J. Biochem.*, 203:33-42.
Holt, C.B., (2003), Substances which Inhibit Ice Nucleation: A Review, *Cryo-Lett.*, 24:269-274.

(Continued)

*Primary Examiner* — John Ulm
(74) *Attorney, Agent, or Firm* — Joseph T. Leone, Esq.; Daniel A. Blasiole; DeWitt Ross & Stevens S.C.

(57) ABSTRACT

Antifreeze polypeptides, antifreeze compositions including the polypeptides, nucleotides encoding the antifreeze polypeptides, methods of making antifreeze compositions, and methods of inhibiting ice crystal growth are provided herein. The peptides are based on the primary sequence of collagen and include those having a molecular weight between about 500-7000 Da. The peptides preferably include cationic polypeptides. The methods of making antifreeze compositions include digesting collagen or gelatin into hydrolysates with peptides having molecular weights between about 500-7000 Da. The digestions are performed with proteases and/or non-enzymatic hydrolysis. The methods of inhibiting ice crystal growth include adding the antifreeze polypeptides or compositions described herein to a composition to be frozen. The methods may be used to inhibit ice crystal growth in frozen food products.

40 Claims, 26 Drawing Sheets

OTHER PUBLICATIONS

Hoshino et al., (2003), Antifreeze proteins from snow mold fungi, *Can. J. Bot.*, 81:1175-1181.

Kay et al., (2000), Evidence for gene transfer and expression of factor IX in haemophilia B patients treated with an AAV vector, *Nat. Genet.*, 24:257.

Kristiansen et al., (2005), The mechanism by which fish antifreeze proteins cause thermal hysteresis, *Cryobiology*, 51:262-280.

Levine et al., (1988), Principles of "Cryostabilization" Technology From Structure/Property Relationships of Carbohydrate/Water Systems—A Review, *Cryo-Lett*, 9:21-63.

Liou et al., (2000), Mimicry of ice structure by surface hydroxyls and water of a B-helix antifreeze protein, *Nature*, 406:322-324.

Miller-Livney et al., (1997), Ice Recrystallization in Ice Cream: Interactions Between Sweeteners and Stabilizers, *J. Dairy Sci.*, 80:447-456.

Muir et al., (1986), Effect of polysaccharide stabilizers on the rate of growth of ice, *J. Food Technol.*, 21:683-689.

Nakai et al., (1998), Adeno-Associated Viral Vector-Mediated Gene Transfer of Human Blood Coagulation Factor IX Into Mouse Liver, *Blood*, 91:4600.

Pentelute et al., (2008), Mirror Image Forms of Snow Flea Antifreeze Protein Prepared by Total Chemical Synthesis Have Identical Antifreeze Activities, *J. Amer. Chem. Soc.*, 130:9702-9707.

Regand et al., (2002), Effect of Biopolymers on Structure and Ice Recrystallization in Dynamically Frozen Ice Cream Model Systems, *J. Dairy Sci.*, 85:2722-2732.

Sarver et al., (1981), Bovine Papilloma virus Deoxyribonucleic Acid: a Novel Eucaryotic Cloning Vector, *Mol. Cell. Biol.*, 1:486.

Sidebottom et al., (2000), Heat-stable antifreeze protein from grass, *Nature*, 406:256.

Simatos et al., (1989), Relation between glass transition and stability of a frozen product, *Cryo-Lett*, 10:77-84.

Wen et al., (1992), A model for binding of antifreeze polypeptide to ice, *Biophys. J.*, 63:1659-1662.

Wigler et al., (1977), Transfer of Purified Herpes Virus Thymidine Kinase Gene to Cultured Mouse Cells, *Cell*, 11:223.

Worral et al., (1998), A Carrot Leucine-Rich-Repeat Protein That Inhibits Ice Recrystallization, *Science*, 282:115-117.

Yang et al., (1998), Identification of the Ice-Binding Surface on a Type III Antifreeze Protein with a "Flatness Function" Algorithm, *Biophys. J.*, 74:2142-2151.

Yeh et al., (1996), Antifreeze Proteins: Structures and Mechanisms of Function, *Chem. Rev.*, 96:601-617.

Zhu et al., (2005), Ice-crystal formation in gelatin gel during pressure shift versus conventional freezing, *J. Food Eng.*, 66:69-76.

\* cited by examiner

Before Thermal Cycling

After Thermal Cycling

Total Hydrolysate

Fraction 1

Fraction 2

Fraction 3

Before Thermal Cycling    After Thermal Cycling 0.5% Fraction 3

2% Fraction 3

Before Thermal Cycling          After Thermal Cycling

Dialysis with 3000 Da cutoff

Before Thermal Cycling          After Thermal Cycling

Elution Profiles of Gelatin hydrolyzates

Control

4% Gelatin Hydrolysate Prepared at pH 5.2

0.5% Gelatin Hydrolysate Prepared at pH 7

1% Gelatin Hydrolysate Prepared at pH 7

Before Thermal Cycling    After Thermal Cycling

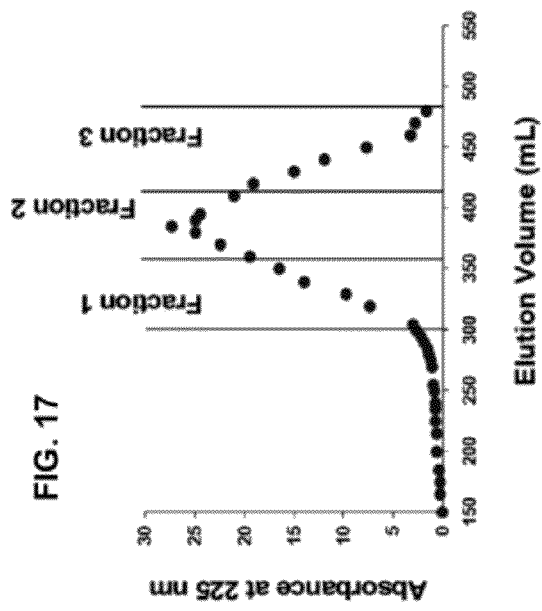
FIG. 17
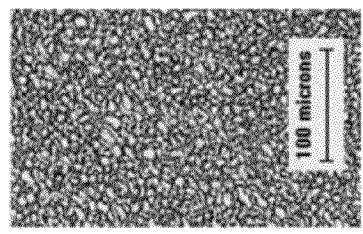
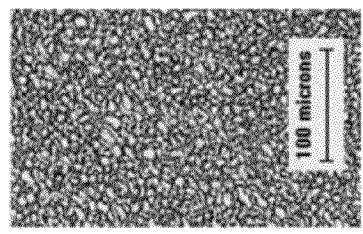
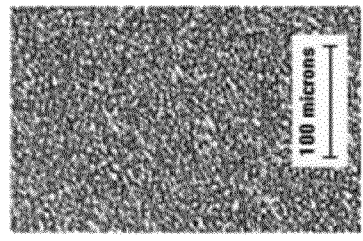
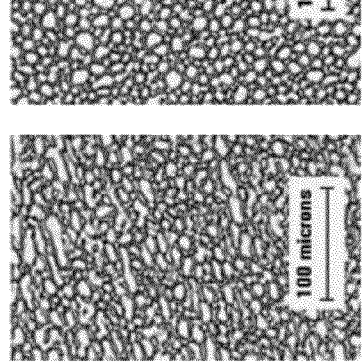

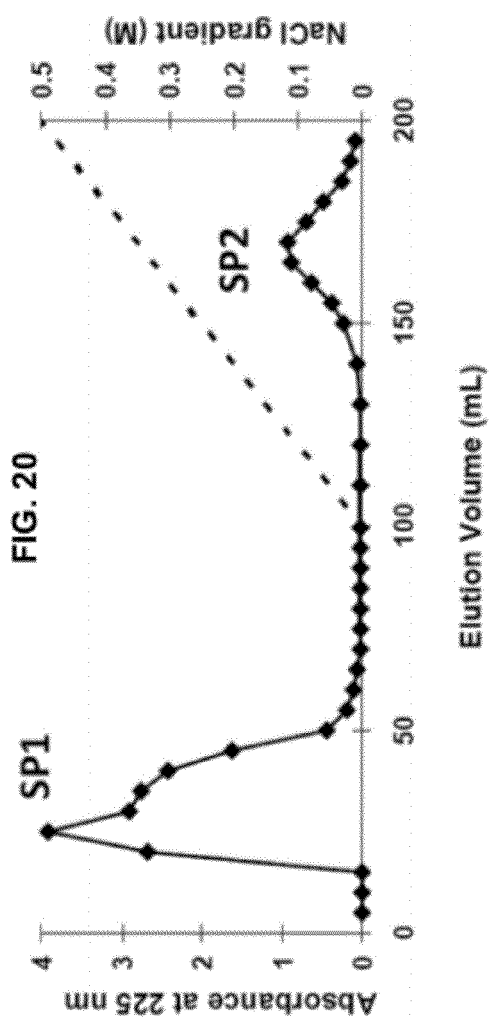
FIG. 20
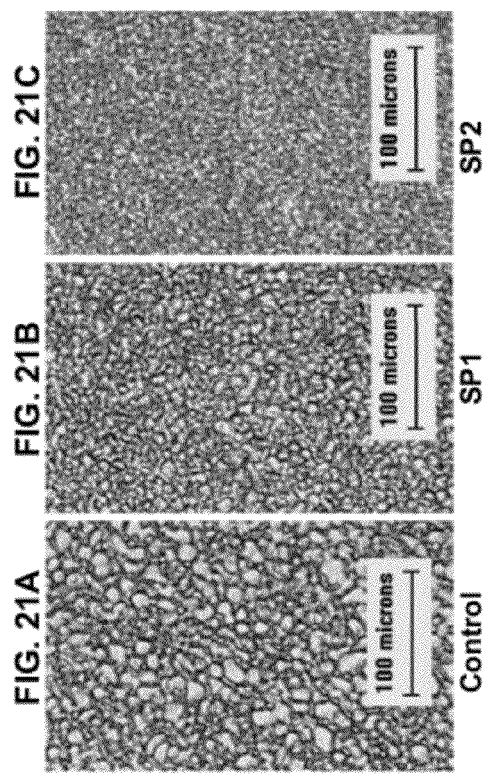
FIG. 21A Control
FIG. 21B SP1
FIG. 21C SP2

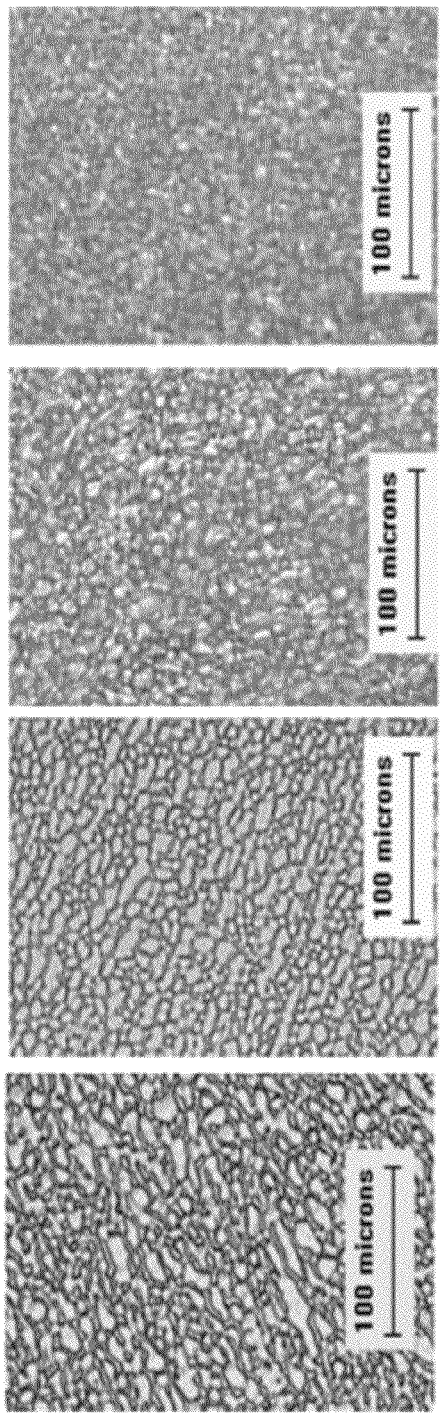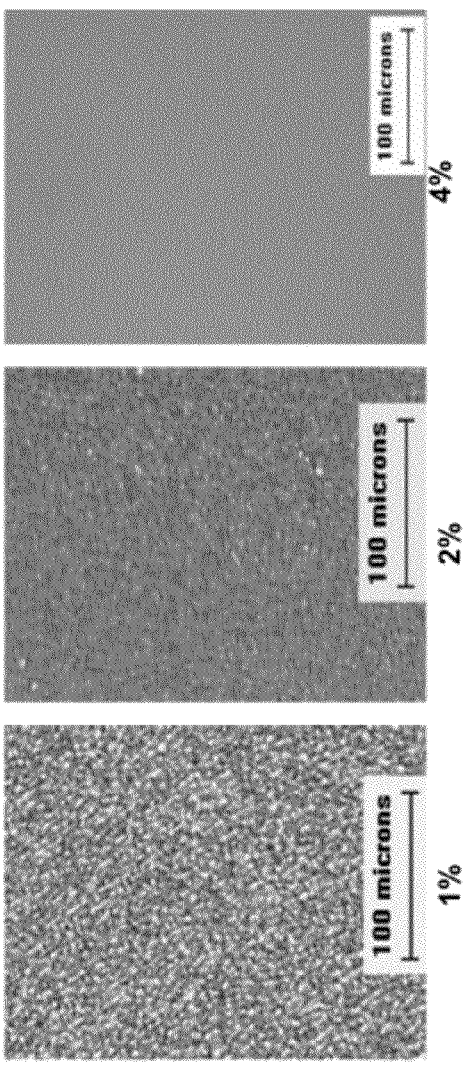

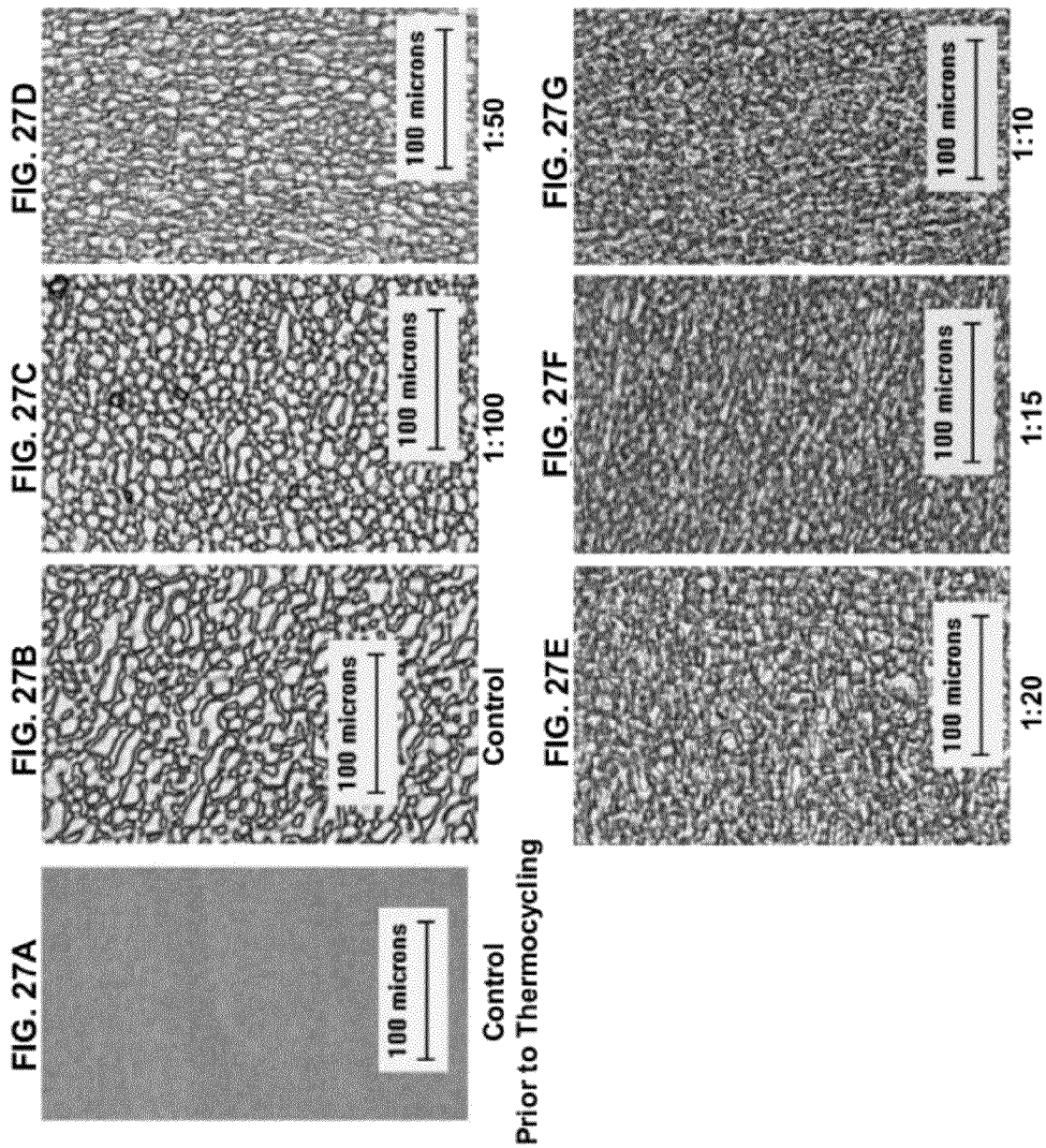

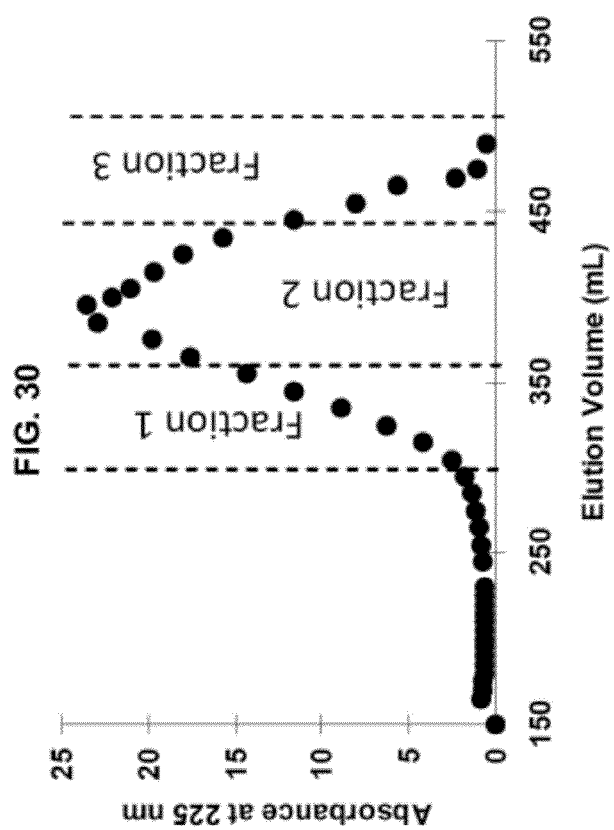
FIG. 30
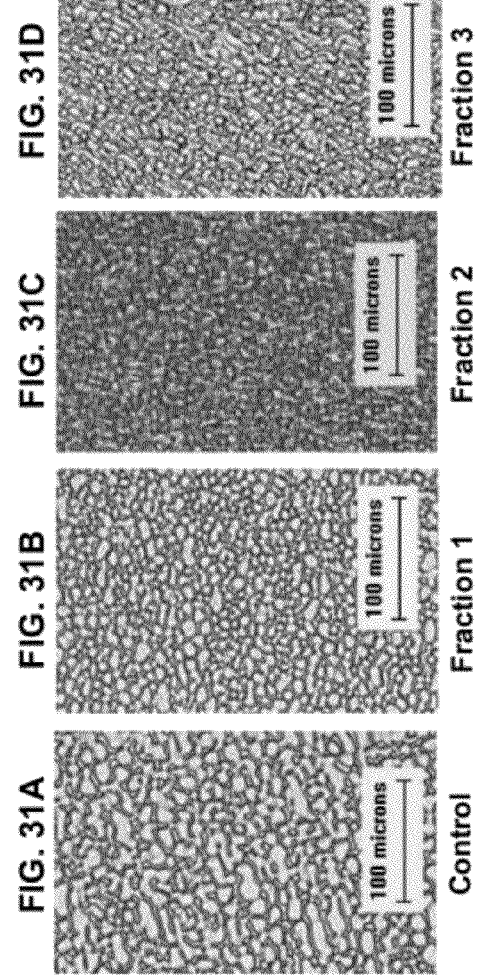
FIG. 31A Control
FIG. 31B Fraction 1
FIG. 31C Fraction 2
FIG. 31D Fraction 3

Control

SP1 fraction

SP2 fraction

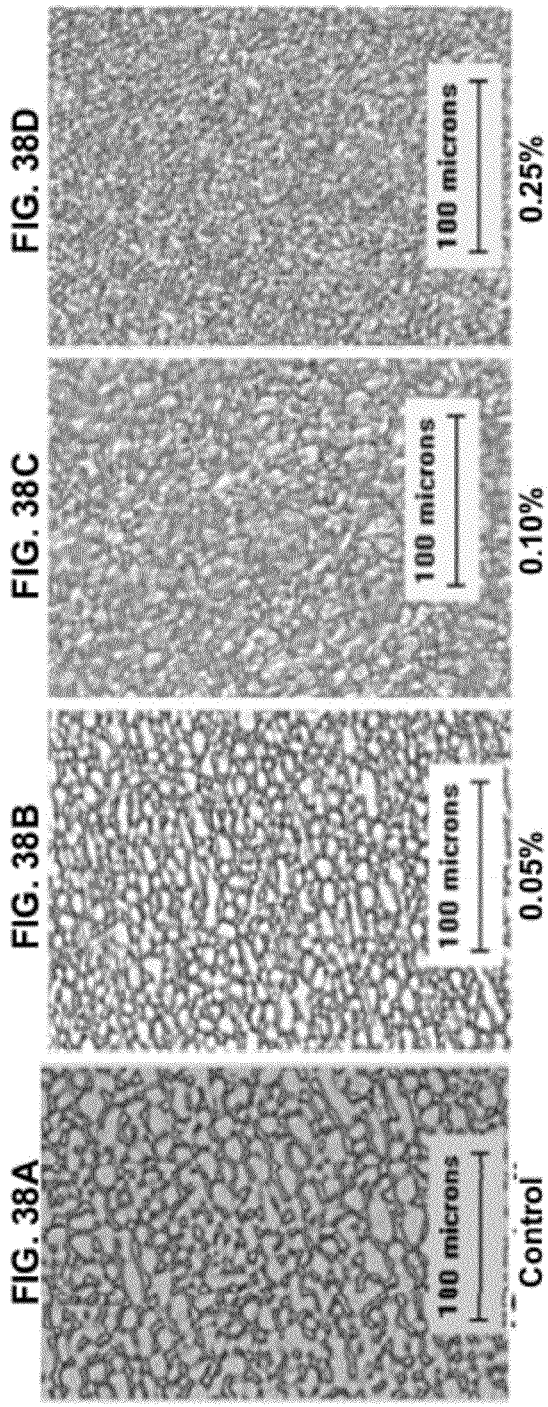
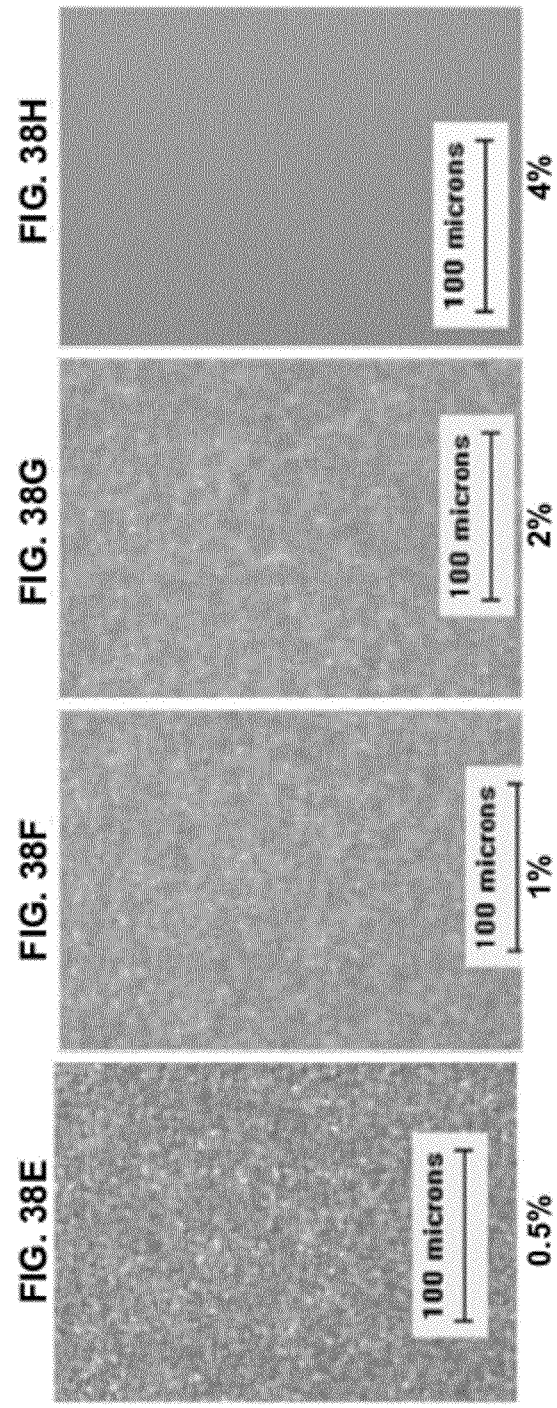

INHIBITION OF ICE CRYSTAL GROWTH

CROSS REFERENCE TO RELATED APPLICATIONS

This application claims priority under 35 USC §119(e) to U.S. Provisional Patent Application 61/118,241 filed Nov. 26, 2008, the entirety of which is incorporated herein by reference.

FIELD OF THE INVENTION

This disclosure generally concerns improvement of foodstuffs subjected to freezing conditions. More particularly, this invention relates to control of ice crystal growth in a frozen foodstuff.

BACKGROUND

Water is one of the major if not the predominant, components of many food products. Consequently, changes in the physical state of water in food systems and/or the extent of its interactions with other food components during storage cause structural and textural changes in foods, which, in some cases, are detrimental to their quality. This is particularly a problem in frozen foods, such as meat, fish, desserts, frozen dough products, and frozen fruits and vegetables (Zhu et al., *J. Food Eng.* 66:69-76 (2005); Regand et al., *J. Dairy Sci.* 85:2722-2732 (2002); Hartel, R. W. Solid-liquid equilibrium: crystallization in foods. In Physical Chemistry of Foods (Schwartzberg, H. G., Hartel, R. W., eds.) Marcel-Dekker, Inc.: New York; 1992, p. 47; Hagiwara et al., *J. Dairy Sci.* 79:735-744 (1996); Arbuckle, W. S. Ice Cream. 4th ed., Van Nostrand Reinhold, New York, N.Y., 1986).

During freezing, which is a process of ice crystallization from super-cooled water, first ice nucleation occurs, followed by ice re-crystallization (Mutaftschiev, B. In Handbook of Crystal Growth, Vol. 1, Hurle, D. T. J., Eds., North Holland Elsevier Science Publishers, Amsterdam, The Netherlands, 1993; pp. 189-247). The size distribution of ice crystals formed during this re-crystallization stage has a strong influence on the texture of frozen foods (Regand et al., *J. Dairy Sci.* 85:2722-2732 (2002); Hartel, R. W. Solid-liquid equilibrium: crystallization in foods. In Physical Chemistry of Foods (Schwartzberg, H. G., Hartel, R. W., eds.) Marcel-Dekker, Inc.: New York; 1992, p. 47) and structural integrity of cell membranes (DeVries, A. L. Survival at freezing temperatures. In Biochemical and Biophysical Perspectives in Marine Biology, Sargent, J. and Mallins, D. W., Eds., Academic Press, London, 1974, pp. 289-330; Beall, P. *Cryobiology* 20:324-224 (1983)).

For instance, although ice crystals in the range of 15-20 μm bestow a desirable smooth texture to ice cream, those that are larger than 40 μm impart an unacceptable coarse and grainy texture to ice cream (Hagiwara et al., *J. Dairy Sci.* 79:735-744 (1996); Arbuckle, W. S. Ice Cream. 4th ed., Van Nostrand Reinhold, New York, N.Y., 1986). Water separation in the form of re-crystallized ice in frozen dough-type products (e.g., frozen pizza, and bread rolls) alters macromolecular interactions in the dough network structure, which results in poor textural quality at the time of baking and consumption.

Temperature fluctuations during storage and handling of frozen foods promote ice crystal growth. The crystal growth rate is very slow at lower storage temperatures, especially when the product is stored below its glass transition temperature (Levine et al., *Cryo-Lett.* 9:21-63 (1988); Simatos et al., *Cryo.-Lett.* 10:77-84 (1989); and Slade et al., *Crit. Rev. Food Sci. Nutr.* 30:115-360 (1991)). For ice cream, the glass transition temperature is typically in the range of −30 to −40° C., depending on the sugar ingredient used (Levine et al., *Agric. Food Chem.* 1:315-396 (1989)). Above the glass transition temperature, the greater molecular mobility of water leads to faster growth of ice crystals. Because the typical average storage temperature in household freezers is well above −20° C. and fluctuates because of automatic defrost cycles (Miller-Livney et al., *J. Dairy Sci.* 80:447-456 (1997)), formation of large ice crystals and deterioration of textural qualities of frozen foods is a common occurrence under household conditions (Fennema, O. *Food Aust.* 45:374 (1993)). Thus, one of the major challenges faced by frozen foods manufacturers is developing appropriate technological conditions and ingredient formulations that can inhibit ice crystal growth during storage and handling.

Previously, it has been found that the addition of hydrocolloids, such as gums and polysaccharides, to frozen foods retards the rate of ice crystal growth (Cornwell, A. S. *Adv. Chem. Ser. Amer. Soc.* 25:59-70 (1960)). The reduced rate of ice crystal growth has been attributed to increased viscosity of the serum phase, which slows down molecular mobility of water (Blond, G. *Cryobiology* 25:61-66 (1988); Budiaman et al., *J. Dairy Sci.* 70:547-554 (1987); Harper et al., *J. Food Sci.* 48:1801-1809 (1983); Flores et al., *J. Dairy Sci.* 82:1399-1407 (1999)). The reduced rate of ice crystal growth has also been attributed to a possible increase of the glass transition temperature (Hagiwara et al., *J. Dairy Sci.* 79:735-744 (1996)). Available evidence indicates that hydrocolloids have no or only a marginal effect on heterogeneous nucleation temperature of supercooled water, but they have a measurable effect on ice crystal growth (Flores et al., *J. Dairy Sci.* 82:1399-1407 (1999)). However, there is no consensus on the mechanism because results from various studies have been contradictory (Flores et al. *J. Dairy Sci.* 82:1399-1407 (1999); Buyong et al., *J. Dairy Sci.* 71:2630-2639 (1988); Goff et al., *J. Dairy Sci.* 76:1268-1275 (1993); Muhr et al., *J. Food technol.* 21:683-689 (1986)).

Several proteins that inhibit ice nucleation have been found in microorganisms (Holt, C. B. *Cryo-Lett.* 24:269-274 (2003); Gilbert et al., *Microbiology* 150:171-180 (2004)), fungi (Hoshino et al., *Can. J. Bot.* 81:1175-1181(2003)), plants (Sidebottom et al., *Nature* 406:256 (2000); Worrall et al., *Science* 282:115-117 (1998)), insects (Graham et al., *Science* 310:461 (2005); Graether et al., *Nature* 406:325-328 (2000)), and fish species (Yeh et al., *Chem. Rev.* 96:601-617 (1996); Chen et al., *Biophys. J.* 77:1602-1608 (1999)).

These antifreeze proteins (AFP), also known as ice structuring proteins (ISP), are polypeptides belonging to structurally diverse families of genetically coded proteins. The fish AFPs are α-helix type, whereas the structure of AFP of cold-tolerant beetles (and other insects) is made of left-handed parallel β-helix containing 15 residues per coil and that of snow fleas is made up of six antiparallel left-handed polyproline type II helices stacked in two sets of three to form a compact structure with a hydrophilic and hydrophobic face. Regardless of their structural diversity, antifreeze proteins from fish, insects, and plants typically contain a rigid flat ice binding face (Liou et al., *Nature* 406:322-324 (2000); Graether et al., *Eur. J. Biochem.* 271:3285-3296 (2004)). This flat face typically contains side chain hydroxyl groups positioned in a two dimensional array that mimics the spacing of oxygen atoms in the hexagonal ice lattice (Pentelute et al., *J. Amer. Chem. Soc.* 130:9702-9707 (2008); Liou et al., *Nature* 406: 322-324 (2000); Wen et al., *Biophys. J.* 63:1659-1662 (1992)). This lattice matching is thought to be fundamental to their ice binding function. Most of the AFPs preferentially bind to the prism faces of ice crystals and inhibit their growth.

The antifreeze activity of AFPs from different sources differs in their effectiveness: Whereas fish AFPs typically depress the freezing point of water by as much as 1° C. (Duman et al., *Biol.* 2:131-182 (1993)), insect AFPs depress the freezing point by more than 5° C. (Graham et al., *Science* 310:461 (2005); Graham et al., *Nature* 388:727-728 (1997)) in a non-colligative manner. However, AFPs do not alter the melting point of ice, which remains at 0° C. The difference between the melting and the freezing temperatures in the presence of these proteins is known as 'thermal hysteresis', and the existence of this thermal hysteresis (TH) is a direct indication of involvement of a non-colligative mechanism (Kristiansen et al., *Cryobiology* 51:262-280 (2005)). In addition to depressing the freezing point, AFPs inhibit ice recrystallization. However, it has been observed that some plant-derived AFPs that show ice recrystallization inhibition (RI) do not exhibit thermal hysteresis (Sidebottom et al., *Nature* 406:256 (2000); Worrall et al., *Science* 282:115-117 (1998)), i.e., they do not necessarily depress the freezing point. From the standpoint of applications in frozen foods and survival function in organisms, the ability to inhibit ice recrystallization, rather than the thermal hysteresis (i.e., depression of freezing point), is the most important desirable function of AFPs (Sidebottom et al., *Nature* 406:256 (2000)).

According to Quick Frozen Foods International (October 2006), the total frozen foods market in the United States was $90.3 billion in 2006, of which the market for ice cream and frozen dessert, fruits, and toppings was about $6.86 billion and that of frozen dough and pizza products was about $6.0 billion. Thus, the frozen foods industry constitutes a significant portion of the total food industry in this country. Ice recrystallization in frozen foods affects the quality of these products. For instance, ice crystals in foods eaten in the frozen state impair their sensory attributes and in frozen dough products (e.g., pizza and other prepared frozen foods) it causes toughening and staling, resulting in poor quality during baking. Because of such ice recrystallization-induced quality changes during frozen storage, each year millions of pounds of frozen products are discarded at the retail and consumer level. The frozen foods industry is faced with the challenge of finding a simple way to inhibit ice recrystallization in frozen food products.

Although antifreeze proteins from fish, plants, and insects that thrive in sub-zero temperature conditions can be potentially used to inhibit ice recrystallization in frozen foods, this is not practical for several reasons: The commercial availability of AFPs is limited and therefore the use of AFPs in frozen foods is not cost-effective. Furthermore, the AFPs are unstable at high temperatures and therefore cannot withstand the blanching operation typically used in frozen fruits and vegetables and pasteurization operation normally used in ice cream manufacture. Therefore, there is a need to develop new antifreeze agents and/or ice recrystallization inhibitors to improve food quality of frozen desserts, dough (e.g., frozen pizza), and fruits and vegetables.

SUMMARY OF THE INVENTION

The invention includes an antifreeze peptide or a mixture of peptides providing inhibition of ice crystal growth in frozen food products. The antifreeze peptide(s) preferably comprises a gelatin (collagen) hydrolysate produced by any protease, including both site specific and non-specific endoproteases (such as papain, ALCALASE, trypsin, V8 protease, etc). The preferred peptides of the gelatin (collagen) hydrolysate have a molecular weight distribution in the range of about 500 Da to about 7000 Da, more preferably in the range of about 600 to about 2800 Da, and most preferably in the range of about 800 Da to about 2500 Da. Hydrolysate fractions containing peptides in the molecular weight range of about 800 Da to about 2500 Da exhibit the highest inhibitory activity on ice crystal growth in frozen foods, such as ice cream mix, whereas fractions containing peptides greater than 7000 Da show reduced inhibition of ice crystal growth. Among the peptides in the preferred ranges, the cationic peptides show higher efficiency of inhibition of ice crystal growth than either the neutral or acidic peptides at pH 7.0.

Various embodiments of the invention include purified antifreeze polypeptides, compositions including the antifreeze polypeptides, and nucleic acids encoding the antifreeze polypeptides. Preferably included in each of the embodiments is a polypeptide between about 500-7000 Da comprising repeating units of the sequence Gly-Z-X, wherein Z and X are any amino acid residue.

In some versions, Z and X in the sequence Gly-Z-X are selected from the group consisting of Ala, Ser, Thr, Pro, Hyp, and Gly.

In other versions, the polypeptide has at least five contiguous residues of SEQ ID NO: 1.

In yet other versions, the polypeptide has a sequence of SEQ ID NO: 1, a variant thereof, and/or a fragment thereof, wherein the variant includes conservative substitutions of residues other than glycine. In particular versions, the variant is at least about 80% identical to SEQ ID NO: 1.

In some versions, the polypeptide has a sequence selected from the group consisting of SEQ ID NO: 3, SEQ ID NO: 5, SEQ ID NO: 7, fragments thereof, and repeating units thereof.

In some versions, the polypeptide is about 600-2800 Da.

In another version, the polypeptide is cationic.

The invention further includes a method of inhibiting ice crystal growth comprising adding to a composition to be frozen any one or combination of the polypeptides or antifreeze compositions described herein.

In some versions, the composition to be frozen is a food product. Preferred food products include ice cream, dough, frozen desserts, frozen pizza, fruits, and vegetables.

In other versions, the polypeptide is added in an amount of at least about 0.1%.

The invention further includes a method of forming gelatin peptides having preferred molecular weight ranges. In a preferred embodiment, the size distribution of gelatin peptides formed in the hydrolysate is controlled by the pH, time and temperature of hydrolysis. Preferably, the hydrolysis conditions for producing peptides with maximum ice crystal growth inhibitory activity is pH 7 at 37° C. for 30 min using an enzyme-to-substrate ratio of 1:10 for crude papain, and pH 9.0 at 45° C. for 30 min using an enzyme-to-substrate ratio of 1:15 for ALCALASE. The optimum pH, temperature, time and the enzyme-to-substrate ratio will vary depending on the enzyme used. For each protease, these conditions should be modified in such a way that the size distribution of peptides in the hydrolysate is in the preferred ranges.

One embodiment of the method includes digesting gelatin or collagen to generate peptides having a molecular weight in a range of about 500-7000 Da.

In some versions, the peptides are fractionated according to molecular weight and those having a molecular weight in the range of about 500-7000 Da are collected.

In other versions, cationic peptides are separated from neutral and anionic peptides, and the cationic peptides are collected.

The digesting includes treating with an enzyme, such as a non-specific protease such as papain, ALCALASE, or combinations thereof, or by performing acid or alkaline hydrolysis.

The digesting is preferably performed at a pH between about 5 and about 9, at a temperature between about 35° C. to about 47° C., and an enzyme-to-gelatin weight ratio of at least 1:50.

The antifreeze peptides and compositions described herein can be used as antifreeze agents and/or ice recrystallization inhibitors to improve food quality of frozen desserts, dough (e.g., frozen pizza), and fruits and vegetables.

The objects and advantages of the invention will appear more fully from the following detailed description of the preferred embodiment of the invention made in conjunction with the accompanying drawings.

BRIEF DESCRIPTION OF THE DRAWINGS

FIG. 8A shows ice cream with 4% dialyzed Fraction 3 at −40° C. before thermal cycling. FIG. 8B shows ice cream with 4% dialyzed Fraction 3 after seven cycles at −14° C. to −12° C.

FIG. 15A shows the control (lacking gelatin hydrolysate) prior to thermal cycling. FIG. 15B shows the control after thermal cycling.

FIG. 17 is a graph showing the elution profile from a Sephadex G-50 column and pooled fractions (Fractions 1, 2, and 3) of gelatin hydrolysates produced from 20% gelatin at pH 7.0 and 37° C. for 30 minutes with a papain-to-gelatin ratio of 1:10.

FIGS. 18A-18D are microscopic images showing the effect of Fraction 1 (FIG. 18B), Fraction 2 (FIG. 18C), and Fraction 3 (FIG. 18D) from FIG. 17 on ice crystal growth in ice cream. The control (FIG. 18A) lacked gelatin hydrolysate.

FIG. 20 is a graph showing the elution profile from ion exchange chromatography of Fraction 2 from FIG. 17 on Sulfopropyl-Sephadex C-25 (SP-Sephadex) using a 0-0.5 M NaCl gradient at pH 7.0.

FIGS. 21A-21C are microscopic images showing the effect of no gelatin hydrolysate (FIG. 21A) and the SP1 (FIG. 21B) and SP2 (FIG. 21C) fractions from FIG. 20 on ice crystal growth in ice cream after thermal cycling.

FIGS. 25A-25G are microscopic images showing the ice crystal growth inhibition activity of the SP3 fraction from FIG. 23, containing the 877 Da peptide, in ice cream mix after seven cycles at −14 to −12° C. at concentration levels of 0% (FIG. 25A), 0.125% (FIG. 25B), 0.25% (FIG. 25C), 0.5% (FIG. 25D), 1% (FIG. 25E), 2% (FIG. 25F), and 4% (FIG. 25G).

FIGS. 27A-27G are microscopic images showing the effects of 4% unfractionated gelatin produced as described for FIG. 26 at 1:100 (FIG. 27C), 1:50 (FIG. 27D), 1:20 (FIG. 27E), 1:15 (FIG. 27F), and 1:10 (FIG. 27G) enzyme-to-substrate ratios after thermal cycling. FIG. 27A shows the control (lacking gelatin hydrolysate) prior to thermal cycling. FIG. 27B shows the control after thermal cycling.

FIG. 30 is a graph showing the elution profile from a Sephadex G-50 column and pooled fractions (Fractions 1, 2, and 3) of gelatin hydrolysates produced from 20% gelatin at pH 9.0 and 45° C. for 30 minutes with a ALCALASE-to-gelatin ratio of 1:15.

FIGS. 31A-31D are microscopic images showing the effect of Fraction 1 (FIG. 31B), Fraction 2 (FIG. 31C), and Fraction 3 (FIG. 31D) from FIG. 30 on ice crystal growth in ice cream. The control (FIG. 31A) lacked gelatin hydrolysate.

FIGS. 38A-38H are microscopic images showing the ice crystal growth inhibition activity of the 2107 Da gelatin peptide from FIG. 37 in ice cream mix after thermal cycling at concentration levels of 0% (FIG. 38A), 0.05% (FIG. 38B), 0.10% (FIG. 38C), 0.25% (FIG. 38D), 0.5% (FIG. 38E), 1% (FIG. 38F), 2% (FIG. 38G), and 4% (FIG. 38H).

DETAILED DESCRIPTION OF THE INVENTION

Figure 1:
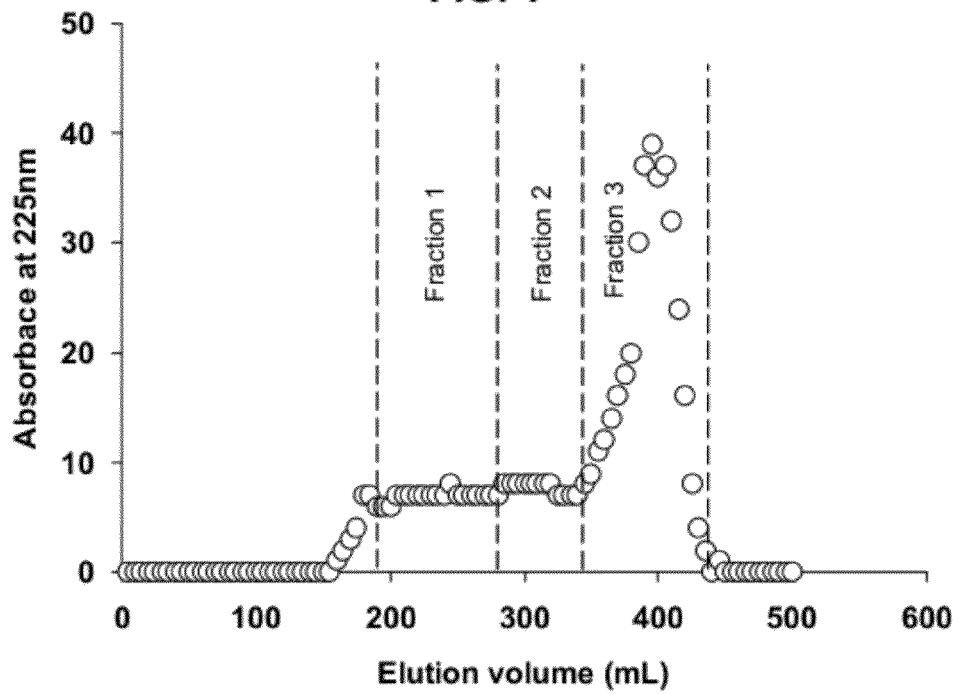
FIG. 1. is a graph showing the elution profile of gelatin hydrolysate on a Sephadex G-50 gel permeation column. Hydrolysis was performed on 20% gelatin (225B40) in 1 M Na2CO3, pH 9.0, containing 10 mM cysteine, for 10 min at 37° C. at a papain-to-gelatin ratio of 1:100. Five milliliter fractions were collected at a flow rate of 2 mL/min.

Peptides that inhibit ice crystal growth in frozen foods and methods of forming gelatin hydrolysates are provided herein.

As used herein, "purified" and "isolated" refer to material that is substantially free from components which normally accompany it in its native state.

The invention includes purified polypeptides having the sequence Gly-Z-X, wherein Z and X are any amino acid residue. In some versions, Z and X can be alanine (Ala), serine (Ser), threonine (Thr), proline (Pro), hydroxyproline (Hyp), and glycine (Gly). Unless otherwise specified, Hyp can be substituted for Pro in any sequence described herein. The Hyp can either be 3-hydroxyproline (3Hyp) or 4-hydroxyproline (4Hyp).

In one version of the invention, the polypeptides have at least 5 contiguous residues, more preferably at least 10 contiguous residues, more preferably at least 15 contiguous residues, and most preferably at least 20 contiguous residues of SEQ ID NO: 1.

The invention includes variants of the sequences described herein. The variants comprise conservative substitutions of amino acids in the sequences described herein. A "conservative substitution" means the replacement of one amino acid by an amino acid having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The variant polypeptides include amino acid sequences with about 50%, 60%, 70%, 75%, 80%, 85%, 90%, 95%, 96%, 97%, 98%, or more identity to the sequences described herein. The term "identity" and grammatical variations thereof, mean that two or more referenced entities are the same. Thus, where two protein sequences are identical, they have the same amino acid sequence. The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403-10 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, and BLOSUM 62.

The invention includes fragments of the polypeptides described herein. "Fragment" means a portion of the full length molecule. For example, a fragment of a given polypeptide is at least one amino acid fewer in length than the full length polypeptide (e.g. one or more internal or terminal amino acid deletions from either amino or carboxy-termini). Fragments therefore can be any length up to, but not including, the full length polypeptide. Suitable fragments of the polypeptides described herein include but are not limited to those having 50%, 60%, 70%, 75%, 80%, 85%, 90%, 95%, 96%, 97%, 98%, or more of the length of the full length polypeptide.

The invention includes polypeptides having repeating units of the sequences described herein. "Repeating units" means a repetition of a given sequence in tandem. Also included are polypeptides having repeating units of fragments of the sequences described herein.

Preferred peptides have a molecular weight in the range of about 500 Da to about 7000 Da, more preferably in the range of about 600 Da to about 2800 Da, and most preferably in the range of about 700 Da to about 2500 Da. Larger and smaller peptides do not inhibit ice crystal growth as effectively as peptides within the preferred molecular weight range. Other effective molecular weights and ranges thereof can be found in the examples described below.

The invention includes cationic polypeptides. A polypeptide that is "cationic" means that the polypeptide can be purified by binding to a cation exchanger by ion exchange chromatography, as described in the examples. "Neutral" and "anionic" polypeptides are those that do not bind to a cation exchanger by ion exchange chromatography.

The invention further includes antifreeze compositions. The antifreeze compositions comprise polypeptides, gelatin hydrolysates, and/or collagen hydrolysates described herein.

The invention further includes isolated nucleic acids encoding the polypeptides described herein and vectors containing the nucleotides. As used herein, "nucleic acid," refers to at least two or more ribo- or deoxy-ribonucleic acid base pairs (nucleotides) linked through a phosphoester bond or equivalent. Nucleic acids include polynucleotides and polynucleosides. Nucleic acids include circular and linear, single, double and triplex molecules. A nucleic acid molecule may belong exclusively to or be in a mixture, but not limited to: RNA, DNA, cDNA, genomic nucleic acid, non-genomic nucleic acid, naturally occurring and non-naturally occurring nucleic acid and synthetic nucleic acid.

The genetic code dictates nucleic acid codons encoding each amino acid. The genetic code is well known in the art. Nucleic acid sequences encoding the polypeptides described herein are therefore easily deduced by practitioners in the art. Exemplary nucleic acid sequences encoding polypeptides described herein include: SEQ ID NO: 2 (encodes SEQ ID NO: 1); SEQ ID NO: 4 (encodes SEQ ID NO: 3); SEQ ID NO: 6 (encodes SEQ ID NO: 5); and SEQ ID NO: 8 (encodes SEQ ID NO: 7). Due to the degeneracy of the genetic code, the nucleic acids of the invention include sequences and subsequences that are degenerate with respect to the nucleic acids explicitly described herein. A start codon (e.g., AUG) and a stop codon (e.g., TAA, TAG, TGA for DNA or equivalents containing uracil (U) for RNA) can be appended to the nucleic acid sequences encoding the polypeptides described herein to generate suitable nucleic acids for producing the polypeptides.

The nucleic acids of the invention further include modifications such as nucleotide and nucleoside substitutions, additions and deletions, as well as derivatized forms and fusion sequences (e.g., encoding chimeric polypeptides).

Nucleic acids can be produced using various standard cloning and chemical synthesis techniques. Such techniques include nucleic acid amplification, e.g., polymerase chain reaction (PCR), with genomic DNA or cDNA targets using primers (e.g., a degenerate primer mixture) capable of annealing to the polypeptide encoding a target sequence. For example, primers specific for desired regions a collagen gene can be used to amplify nucleic acids of the invention from a genomic DNA template. The primers may further include start codons, stop codons, and/or restriction sites for cloning the amplified DNA into a vector. Alternatively, nucleic acids of the present invention with the above genetic elements may be chemically synthesized as described in U.S. Pat. No. 6,040,439, incorporated herein by reference in its entirety. The produced nucleic acids can then be translated in vitro, or cloned into a plasmid and propagated and then expressed in a cell (e.g., microorganism, such as yeast or bacteria, a eukaryote such as an animal or mammalian cell or in a plant). Detailed protocols for such molecular biological techniques can be found in Sambrook et al., In: *Molecular Cloning: A Laboratory Manual*, 3$^{rd}$ ed., Cold Spring Harbor Laboratory Press, 2001); and Ausubel et al., *Current Protocols in Molecular Biology*, Greene Publishing Assoc. and Wiley Interscience, N.Y., 1989.

The invention further provides expression cassettes including a nucleic acid encoding a polypeptide as described herein operably linked to an expression control element. The term "operably linked" refers to a physical or functional relationship between the elements referred to that permit them to operate in their intended fashion. Thus, an expression control element "operably linked" to a nucleic acid means that the control element modulates nucleic acid transcription and, as appropriate, translation of the transcript.

Physical linkage is not required for the elements to be operably linked. For example, a minimal element can be linked to a nucleic acid encoding a polypeptide of the invention. A second element that controls expression of an operably linked nucleic acid encoding a protein that functions "in trans" by binding to the minimal element can influence expression of the polypeptide. Because the second element regulates expression of the polypeptide, the second element is operably linked to the nucleic acid encoding the polypeptide even though it is not physically linked.

The term "expression control element" refers to a nucleic acid element that influences expression of an operably linked nucleic acid. Promoters and enhancers are particular non-limiting examples of expression control elements. A "promoter sequence" is a regulatory region capable of initiating transcription of a downstream (3' direction) coding sequence. The promoter sequence includes nucleotides for facilitating transcription initiation. Enhancers also regulate gene expression, but can function a distance from the transcription start site of the gene to which it is operably linked (e.g., at either 5' or 3' ends of the gene, as well as within the gene). Additional expression control elements include leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of a gene of interest, and stop codons.

Expression control elements include "constitutive" elements such that transcription of the operably linked nucleic acid occurs without a signal or stimuli. Expression control elements that confer expression in response to a signal or stimuli, which either increases or decreases expression of the operably linked nucleic acid, are "regulatable." A regulatable element that increases expression of the operably linked nucleic acid in response to a signal or stimuli is referred to as an "inducible element." A regulatable element that decreases expression of the operably linked nucleic acid in response to a signal or stimuli is referred to as a "repressible element" (i.e., the signal decreases expression; when the signal is removed or absent, expression is increased).

Expression control elements include elements active in a particular tissue or cell type, and are referred to as "tissue-specific" expression control elements. Tissue-specific expression control elements are typically active in specific cell or tissue types because they are recognized by transcriptional activator proteins, or other regulators of transcription, that are unique to the specific cell or tissue type.

Expression control elements include full-length nucleic acid sequences, such as native promoter and enhancer elements, as well as subsequences or nucleotide variants thereof (e.g., substituted/mutated or other forms that differ from native sequences) which retain all or part of full-length or non-variant control element function (confer regulation, e.g., retain some amount of inducibility in response to a signal or stimuli).

For bacterial expression, constitutive promoters include T7, as well as inducible promoters such as pL of bacteriophage λ, plac, ptrp, ptac (ptrp-lac hybrid promoter). In insect cell systems, constitutive or inducible promoters (e.g., ecdysone) may be used. Other examples of insect cell promoters include the p10 promoter and the polyhedrin promoter. In yeast, constitutive promoters include, for example, ADH or LEU2 and inducible promoters such as GAL (see, e.g., Ausubel et al., In: *Current Protocols in Molecular Biology*, Vol. 2, Ch. 13, ed., Greene Publish. Assoc. & Wiley Interscience, 1988; Grant et al., (1987) In: *Methods in Enzymology*, 153:516-544, eds. Wu & Grossman, 1987, Acad. Press, N.Y.; Glover, *DNA Cloning*, Vol. 11, Ch. 3, IRL Press, Wash., D.C., 1986; Bitter (1987) In: *Methods in Enzymology*, 152: 673-684, eds. Berger & Kimmel, Acad. Press, N.Y.; Strathern et al., *The Molecular Biology of the Yeast Saccharomyces* (1982) eds. Cold Spring Harbor Press, Vols. I and II; and Sambrook et al., *Molecular Cloning: A Laboratory Manual*, 3$^{rd}$ ed., Cold Spring Harbor Laboratory Press, 2001).

For mammalian expression, constitutive promoters of viral or other origins may be used. For example, SV40, or viral long terminal repeats (LTRs) and the like, or inducible promoters derived from the genome of mammalian cells (e.g., metallothionein IIA promoter; heat shock promoter, steroid/thyroid hormone/retinoic acid response elements) or from mammalian viruses (e.g., the adenovirus late promoter; the inducible mouse mammary tumor virus LTR) are used.

The invention also provides stably and transiently transformed cells and progeny thereof, where progeny includes all descendent cells, into which a nucleic acid molecule encoding a polypeptide of the invention has been introduced by means of recombinant DNA techniques in vitro, ex vivo or in vivo. The transformed cells can be propagated and the introduced nucleic acid transcribed, or encoded protein expressed. Transformed cells include but are not limited to prokaryotic and eukaryotic cells such as bacteria, fungi, plant, insect, and animal (e.g., mammalian, including human) cells. The cells may be present in culture, in tissue or an organ ex vivo, or in a subject or patient. A progeny cell may not be identical to the parental cell, since there may be mutations that occur during parental cell replication.

The term "transformed" means a change in a cell following incorporation of nucleic acid (e.g., a transgene) or protein exogenous to the cell. Thus, "transformed cells" include cells into which, or a progeny of which, a nucleic acid or polypeptide has been introduced by means of recombinant DNA techniques. Cell transformation to produce such cells may be carried out as described herein or using techniques known in the art. Accordingly, methods of producing cells including the nucleic acids and polypeptides of the invention are also provided.

Typically, cell transformation with a nucleic acid employs a "vector," which refers to a plasmid, virus, such as a viral vector, or other vehicle known in the art that can be manipulated by insertion or incorporation of a nucleic acid sequence. For genetic manipulation "cloning vectors" can be employed, and to transcribe or translate the inserted polynucleotide "expression vectors" can be employed. Such vectors are useful for introducing nucleic acids, including a nucleic acid that encodes a polypeptide described herein operably linked with an expression control element, and expressing the polypeptide in vitro (e.g., in solution or in solid phase), in cells.

A vector generally contains an origin of replication for propagation in a cell. Control elements, including expression control elements as set forth herein, present within a vector, can be included to facilitate transcription and translation.

Vectors can include a selection marker, which is a gene that allows for the selection of cells containing the gene. "Positive selection" refers to a process whereby only cells that contain the selection marker will be selected. Drug resistance is one example of a positive selection marker; cells containing the marker will survive in culture medium containing the selection drug, and cells lacking the marker will die. Selection markers include drug resistance genes such as neo, which confers resistance to G418; hygr, which confers resistance to hygromycin; and puro, which confers resistance to puromycin. Other positive selection marker genes include genes that allow identification or screening of cells containing the marker. These genes include genes for fluorescent proteins (GFP and GFP-like chromophores, luciferase), the lacZ gene, the alkaline phosphatase gene, and surface markers such as CD8, among others. "Negative selection" refers to a process whereby cells containing a negative selection marker are not selected, for example, due to exposure to an appropriate negative selection agent. For example, cells which contain the herpes simplex virus-thymidine kinase (HSV-tk) gene (Wigler et al., *Cell* 11:223 (1977)) are sensitive to the drug gancyclovir (GANC). Similarly, the gpt gene renders cells sensitive to 6-thioxanthine. Vectors can also include an amplification marker such as the gene providing resistance to methotrexate (see e.g., U.S. Pat. No. 5,179,017), or the CAD gene (see, e.g., Wahl et al., *Somat. Cell Mol. Genet.* 12:339 (1986).

Viral vectors included are those based on retroviral, adeno-associated virus (AAV), adenovirus, reovirus, lentivirus, rotavirus genomes, simian virus 40 (SV40) or bovine papilloma virus (Cone et al., *Proc. Natl. Acad. Sci. USA* 81:6349 (1984); Eukaryotic Viral Vectors, Cold Spring Harbor Laboratory, Gluzman ed., 1982; Sarver et al., *Mol. Cell. Biol.* 1:486 (1981)). Additional viral vectors useful for expression include parvovirus, rotavirus, Norwalk virus, coronaviruses, paramyxo and rhabdoviruses, togavirus (e.g., sindbis virus and semliki forest virus) and vesicular stomatitis virus (VSV).

Mammalian expression vectors include those designed for in vivo and ex vivo expression, such as AAV (U.S. Pat. No. 5,604,090). AAV vectors have previously been shown to provide expression of Factor IX in humans and in mice (Kay et al., *Nat. Genet.* 24:257 (2000); Nakai et al., *Blood* 91:4600 (1998)). Adenoviral vectors (U.S. Pat. Nos. 5,700,470, 5,731, 172 and 5,928,944), herpes simplex virus vectors (U.S. Pat. No. 5,501,979), retroviral vectors (e.g., lentivirus vectors are useful for infecting dividing as well as non-dividing cells and foamy viruses) (U.S. Pat. Nos. 5,624,820, 5,693,508, 5,665, 577, 6,013,516 and 5,674,703 and WIPO publications WO92/05266 and WO92/14829) and papilloma virus vectors (e.g., human and bovine papilloma virus) have all been employed (U.S. Pat. No. 5,719,054). Vectors also include cytomegalovirus (CMV) based vectors (U.S. Pat. No. 5,561, 063). Vectors that efficiently deliver genes to cells of the intestinal tract have been developed (see, e.g., U.S. Pat. Nos. 5,821,235, 5,786,340 and 6,110,456).

Introduction of nucleic acids into target cells can also be carried out by methods known in the art such as osmotic shock (e.g., calcium phosphate), electroporation, microinjection, cell fusion, etc. Introduction of nucleic acids in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. Nucleic acids can be entrapped in microcapsules prepared by coacervation techniques or by interfacial polymerization, for example, by the use of hydroxymethylcellulose or gelatin-microcapsules, or poly(methylmethacrolate)microcapsules, respectively, or in a colloid drug delivery system. Colloidal dispersion systems include macromolecule complexes, nano-capsules, microspheres, beads, and lipid-based systems, including oil-in-water emulsions, micelles, mixed micelles, and liposomes.

The invention further provides methods of making an anti-freeze composition containing antifreeze gelatin hydrolysates. The gelatin hydrolysates are preferably formed using type 225B40 gelatin from bovine hyde (available from several commercial sources) and a protease. Other gelatins can be used. Gelatins such as 60 bloom and 125 bloom gelatins produce smaller peptides than the type 225B40 gelatin under the hydrolysis conditions described below. Thus, it is necessary to optimize the hydrolysis conditions discussed below when using 60 bloom or 125 bloom gelatin to obtain a gelatin hydrolysate having the preferred molecular weights. Collagen can also be used to produce the gelatin hydrolysates using similar conditions.

Any protease can be used to form the gelatin hydrolysate. Preferred proteases are selected from the group consisting of ALCALASE, papain, and/or combinations thereof.

The hydrolysate can also be obtained by acid or alkaline hydrolysis of gelatin or collagen (bovine hyde) under conditions that produce a hydrolysate having the preferred molecular weights. This could also include commercial gelatin preparations or fractions having the preferred molecular weights.

In the preferred version, the protease is papain, such as papain (EC 3.4.22.2) from papaya latex or a subtilisin such as "ALCALASE"-brand protease from *Bacillus licheniformis* (Novozymes, Denmark) (EC 3.4.21.62, formerly EC 3.4.21.16 and included in EC 3.4.21.14) (available from Sigma Chemicals, Co., St. Louis, Mo.). Papain is a nonspecific protease with an optimum pH in the range of about 6 to about 7 and optimum temperature at about 65° C. ALCALASE also is a nonspecific enzyme with an optimum pH in the range of about 6.5 to about 8.5 and an optimum temperature of about 60° C. The products of hydrolysis of gelatin by papain and ALCALASE generally consist of peptides with a range of molecular weights, and the molecular weight distribution of the peptides produced can be manipulated by varying the pH, temperature, time of hydrolysis, and the enzyme to gelatin weight ratio in the reaction.

According to Sigma Chemicals Co., the specific activity of papain used herein was 2.3 units/mg. One unit of enzyme is defined as hydrolysis of 1 µmol of benzoyl-L-arginine ethyl ester (BAEE) substrate per min at pH 6.2 at 25° C. The ALCALASE enzyme used was in a solution form with a specific activity of 2.64 Anson units/g solution. According to the supplier (Sigma Chemical Co.), one Anson unit of enzyme is defined as the amount of enzyme that digests and liberates an amount of TCA-soluble product per minute which gives the same color with Folin-Ciocalteu phenol reagent as one milliequivalent of tyrosine at 25° C. at pH 7.5.

In general, the hydrolysis of gelatin or collagen is carried out at a pH of about 5 to 9, and a temperature between about 35° C. and 47° C. Specifically, the pH of hydrolysis is about 6 to about 8 when using papain or about 5 to about 9 when using ALCALASE. For example, when using ALCALASE, the gelatin is hydrolyzed at pH 9 at about 45° C. for about 30 min and an ALCALASE-(solution as obtained from Sigma Chemical Co.)-to-gelatin ratio of about 1:15 to obtain a gelatin hydrolysate having a molecular weight ranging from about 700 Da to about 3000 Da. When using papain, the gelatin is hydrolyzed at pH 7 at about 37° C. for about 30 min and a papain-(solid as obtained from Sigma Chemical Co.)-to-gelatin ratio of about 1:10 to obtain a gelatin hydrolysate having a molecular weight ranging from about 700 Da to about 3000 Da.

The methods of generating antifreeze compositions may further include a step of fractionating the peptides according to molecular weight and collecting peptides having a specific molecular weight. An exemplary form of such "fractionating" and "collecting" is performed by the use of chromatography using a gel filtration column as described in the examples. However, "fractionating" and "collecting" includes any method of purifying peptides having the preferred molecular weights known in the art.

The methods of generating antifreeze compositions may further include a step of separating cationic peptides from neutral and anionic peptides and a step of collecting the cationic peptides. An exemplary form of such "separating" and "collecting" is performed by the use of cation exchange chromatography as described in the examples. However, "separating" and "collecting" includes any method of purifying cationic peptides known in the art.

The peptides and hydrolysates described herein can be used in various frozen foods, including frozen desserts, dough (e.g., frozen pizza), fruits, vegetables, and ice cream.

METHODS USED IN EXAMPLES

Gelatin hydrolysate: To form the gelatin hydrolysate, a solution of gelatin was hydrolyzed using an enzyme under conditions stated in each of the following examples. Hydrolysis was stopped by incubating the solution for 10 min in boiling water. The gelatin hydrolysate was fractionated on a Sephadex G-50 gel permeation column (100 cm length and 2.6 cm diameter) using water at pH 7.0 as the eluent. Five milliliter fractions were collected at a flow rate of 2 mL/min. The elution profile was determined by measuring the absorbance at 225 nm using a spectrophotometer. The tubes corresponding to various molecular weight ranges were pooled and lyophilized.

The protein content of lyophilized samples was determined by the Biuret method using bovine serum albumin as the standard. The molecular weight versus elution volume relationship of the Sephadex G-50 column was calibrated using alpha-lactalbumin (14.200 Da), myoglobin (17,000 Da), trypsin inhibitor (20,100 Da), trypsinogen (24,000 Da), and carbonic anhydrase (29,000 Da). The void volume of the column was determined using blue dextran. The molecular weight versus elution volume (Ve) relationship followed eq 1.

$$\log MW = -0.0034 V_e + 5.03 \tag{1}$$

Equation 1 was used to estimate the apparent molecular weight (MW) range of the gelatin hydrolysate fractions.

Samples: In all the following examples, an ice cream mix from a local commercial source having the following composition was used: 12.0% milk fat in the emulsified form, 11.0% nonfat milk solids, 16.0% sucrose, 0.1% emulsifier; and the rest as water. The original ice cream mix was first diluted 15 wt % with water to bring the total non-fat solids to 23%. To this was added up to 4% gelatin hydrolysate as nonfat solids so that the maximum non-fat solids was 27%. All experiments were conducted on a single batch of ice cream mix, which was stored at −20° C. in 2 mL aliquots in cryovials. Samples from one vial were used for each set of experiments, and the unused portion was discarded.

Ice recrystallization inhibition assay: Ice recrystallization inhibition activity of gelatin hydrolysates (and their fractions) in ice cream mix and/or in 23% sucrose solution was studied using a cold stage (model THMS600, Linkham Scientific Instruments, Ltd., Surrey UK; or model HCS302, Instec Scientific Instruments Ltd., Boulder, Colo., U.S.A;) mounted on either a Leitz Laborlux S microscope (W. Nuhsbaum, Inc., McHenry, Ill.) or a Nikon Eclipse microscope (E200, Nikon Inc., Japan). The images were captured using a charge-coupled device (CCD) camera and analyzed using Image-Pro Plus software (Media Cybernetics, Silver Spring, Md., U.S.A). In a typical experiment, a small drop (5 µL) of ice cream or sucrose solution (with or without gelatin hydrolysate) was placed on a microscope glass slide, covered with a glass cover slip, placed inside the thermal stage, and quickly frozen by decreasing the temperature from ambient to −40° C. at the rate of 40° C./min. The sample was held at −40° C. for 5 min, and a microscopic image of the sample at −40° C. was recorded. The temperature of the sample was then increased from −40 to −14° C. at the rate of 1° C./min and then cycled between −14 and −12° C. at a rate of about 1 cycle per about 3 min. During such cooling and warming processes, the sample is first converted to a glass at −40° C. and as the sample is slowly warmed up to −14° C. (i.e., above its glass transition temperature), it undergoes irruptive recrystallization of ice, producing a cloud of ice nuclei or very fine ice crystals, which further grows during thermal cycling between −14 to −12° C.

A decrease in the number as well as the size of ice crystals in the presence of gelatin peptides after a given number of thermal cycles is indicative of the peptides' ability to inhibit ice recrystallization. In these studies, seven cycles were employed because these temperature cycling conditions represent approximately one to two-month storage of ice cream in a typical household freezer. Microscopic images of the sample were recorded at the end of seven cycles at a magnification of 220×. The average size of ice crystals formed after seven cycles was determined using the Image-Pro Plus software (Media Cybernetics, Silver Spring, Md., U.S.A).

The following examples are exemplary and are not meant to limit any aspects of the embodiments disclosed herein.

Example 1

In this example, a gelatin hydrolysate was obtained by hydrolyzing a 20 wt % solution of gelatin in 1 M $Na_2CO_3$ containing 10 mM cysteine using papain at 37° C. and pH 9.0 for 10 min at an enzyme-to-gelatin weight ratio of 1:100.

FIG. 1 shows the elution profile of gelatin hydrolysate. Based on equation 1 (shown above), the molecular weight of peptides in the hydrolysate ranged from approximately 3,200 to 22,400 Da.

The 5 mL fractions were pooled into three major fractions (Fractions 1-3) according to decreasing molecular weight, and the pooled fractions were lyophilized. It should be noted that the viscosity of 4% gelatin hydrolysate in water was less than about 1.3 mPa·s, and therefore the effect of the 4% gelatin hydrolysate on the viscosity of the ice cream mix is assumed to be negligible.

Figure 2A:
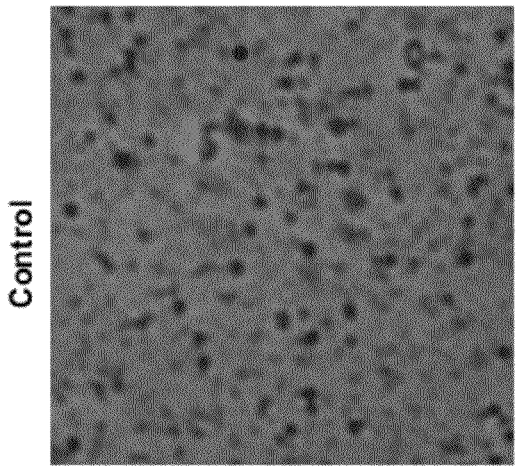
FIGS. 2A and 2B are microscopic images showing the effect of ice crystal growth in ice cream not including a gelatin hydrolysate before (FIG. 2A) and after (FIG. 2B) thermal cycling.
Figure 2B:
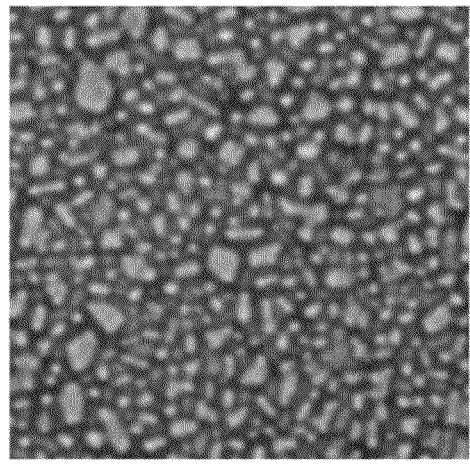

FIGS. 2A and 2B show the effect of ice crystal growth on a control sample of the ice cream. FIG. 2A shows that control ice cream at about −40° C. before thermal cycling, while FIG. 2B shows the ice crystal growth after seven thermal cycles between about −14° C. and about −12° C. The change in texture of the control sample after thermal cycling is apparent in FIG. 2B.

Figure 3A:
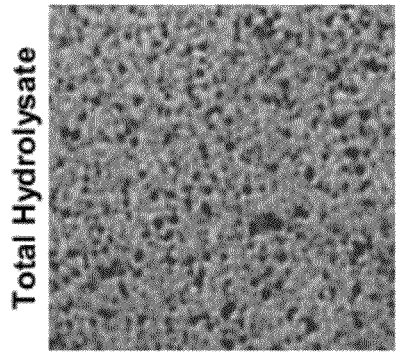
FIGS. 3A and 3B are microscopic images showing the effect of 4% total gelatin hydrolysate on ice crystal growth in ice cream before (FIG. 3A) and after (FIG. 3B) thermal cycling.
Figure 3B:
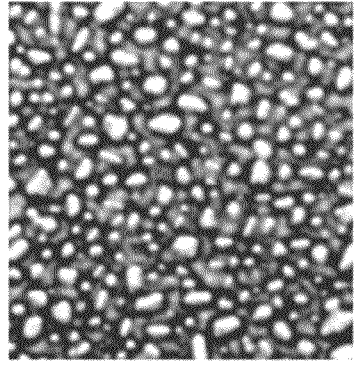

FIGS. 3A and 3B compare the effect of the total hydrolysate (i.e., unfractionated) before (FIG. 3A) and after (FIG. 3B) seven thermal cycles between about −14° C. and about −12° C. At the 4 wt % level, the total gelatin hydrolysate was unable to inhibit ice crystal growth in ice cream mix during thermal cycling.

Figure 4A:
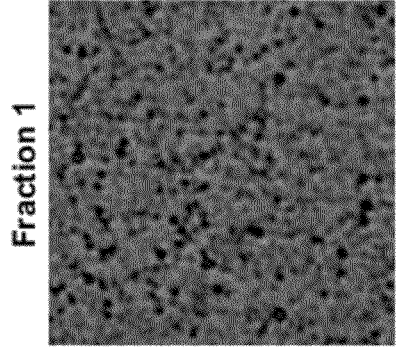
FIGS. 4A and 4B are microscopic images showing the effect of 4% Fraction 1 on ice crystal growth in ice cream before (FIG. 4A) and after (FIG. 4B) thermal cycling.
Figure 4B:
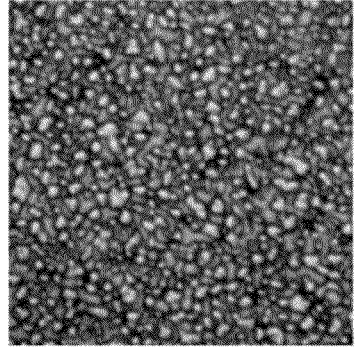

FIGS. 4A and 4B show the effect of 4% Fraction No. 1 on ice crystal growth in ice cream mix before (FIG. 4A) and after (FIG. 4B) seven thermal cycles between about −14° C. and about −12° C. As shown, Fraction No. 1 was unable to completely inhibit ice crystal growth in ice cream after thermal cycling, though the size of the ice crystals is smaller than those in the control with no added gelatin hydrolysate (compare to FIG. 2B).

Figure 5A:
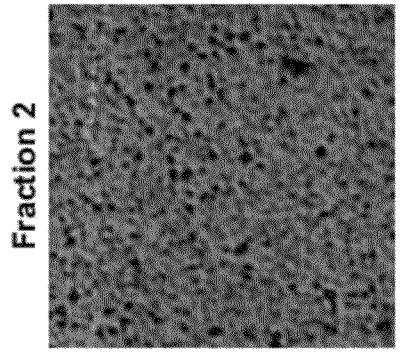
FIGS. 5A and 5B are microscopic images showing the effect of 4% Fraction 2 on ice crystal growth in ice cream before (FIG. 5A) and after (FIG. 5B) thermal cycling.
Figure 5B:
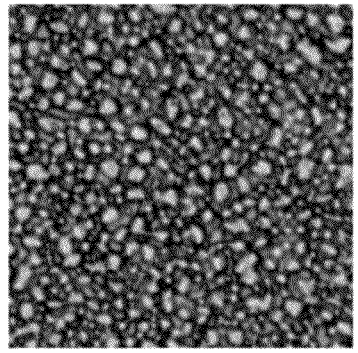

FIGS. 5A and 5B show the effect of 4% Fraction No. 2 on ice crystal growth in ice cream mix before (FIG. 5A) and after (FIG. 5B) seven thermal cycles between about −14° C. and about −12° C. As shown, Fraction No. 2 was also unable to completely inhibit ice crystal growth in ice cream after thermal cycling, though the size of the ice crystals is smaller than those in the control with no added gelatin hydrolysate (compare to FIG. 2B).

Figure 6A:
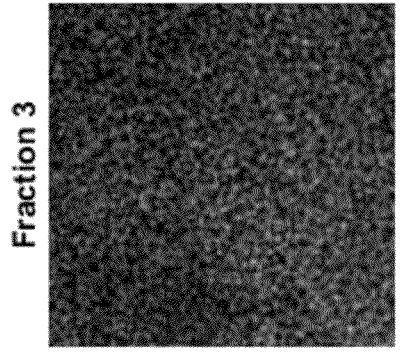
FIGS. 6A and 6B are microscopic images showing the effect of 4% Fraction 3 on ice crystal growth in ice cream before (FIG. 6A) and after (FIG. 6B) thermal cycling.
Figure 6B:
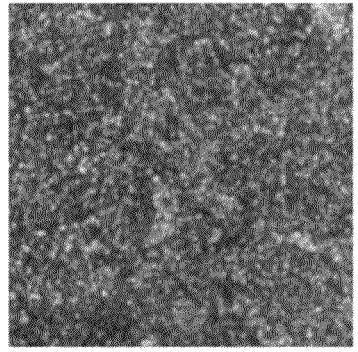
Figure 7A:
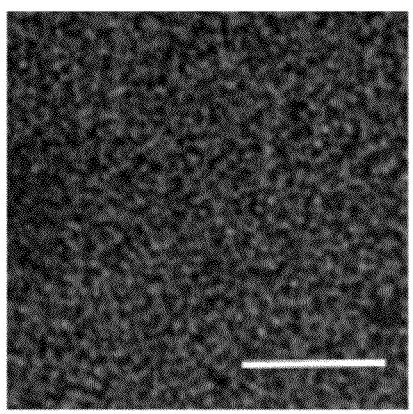
FIGS. 7A and 7B are microscopic images showing the effect of 0.5% Fraction 3 on ice crystal growth in ice cream before (FIG. 7A) and after (FIG. 7B) thermal cycling.
Figure 7B:
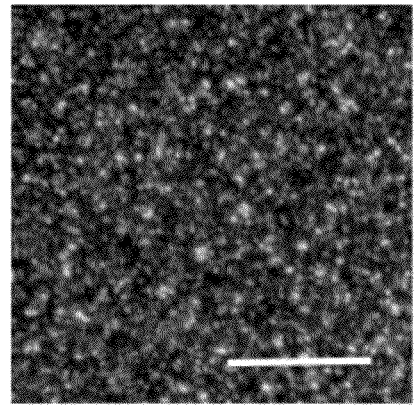
Figure 7C:
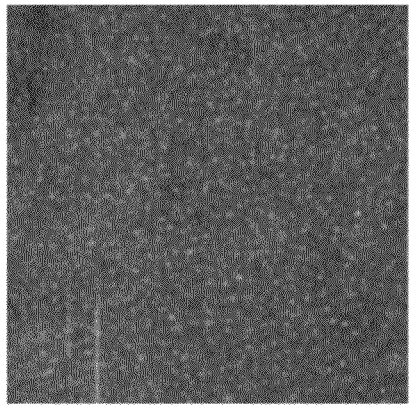
FIGS. 7C and 7D are microscopic images showing the effect of 2.0% Fraction 3 on ice crystal growth in ice cream before (FIG. 7C) and after (FIG. 7D) thermal cycling.
Figure 7D:
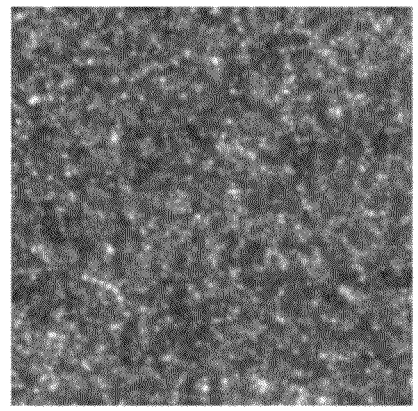
Figure 8A:
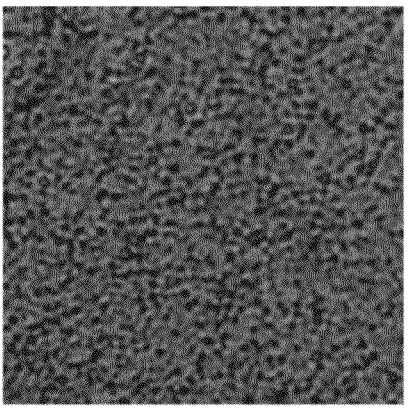
FIGS. 8A and 8B are microscopic images showing the effect of dialysis (3000 Da nominal cutoff membrane) on the inhibitory activity of Fraction 3 on ice crystal growth in ice cream.
Figure 8B:
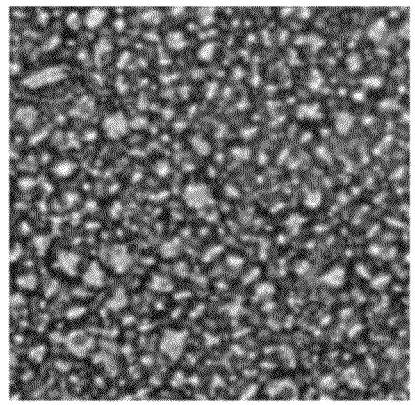

In contrast, as shown in FIGS. 6A and 6B, 4% Fraction 3 was very effective in inhibiting ice crystal growth. Fraction 3 was also effective in inhibiting ice crystal growth even at the 0.5 wt % level, as shown in FIGS. 7A and 7B. As shown in FIGS. 8A and 8B, Fraction 3 also effectively inhibited ice crystal growth at the 2% level.

Taken together, the results shown in FIGS. 1 through 8B indicate that gelatin polypeptides greater than about 7000 Da had poor ability to inhibit ice crystal growth in ice cream mix, whereas polypeptides with molecular weights less than about 7000 Da possessed inhibitory activity on ice crystal growth.

To determine if peptides smaller than about 3000 Da were relevant for the inhibitory effect of Fraction No. 3 on ice crystal growth, Fraction No. 3 was dialyzed overnight against water using a 3000 Da nominal molecular weight cutoff dialysis membrane. The retentate was lyophilized and its inhibitory activity on ice crystal growth was checked.

As shown in FIGS. 8A and 8B, the removal of peptides smaller than about 3000 Da eliminated the inhibitory activity of Fraction No. 3 on ice crystal growth, which strongly suggests that the antifreeze properties of gelatin hydrolysate might arise predominantly from peptides smaller than about 3000 Da. It should be noted, however, that a 3000 Da nominal molecular weight cutoff dialysis membrane would permit, to some extent, leaching of peptides in the 3000 to 4000 Da range, and it is therefore possible that some peptides in the 3000 to 4000 Da range also might possess inhibitory activity on ice crystal growth.

Example 2

To further confirm if the molecular size of gelatin peptides was critical for their inhibitory effect on ice crystal growth, a second sample was prepared. Papain digestion of gelatin was performed in water at pH 5.2 and at pH 7.0, 20% gelatin (type 225B40) in water, temperature 37° C. at a hydrolysis time of about 10 minutes and a papain-to-gelatin ratio of 1:100 to generate peptides with different molecular weight distribution profiles. After digestion and inactivation of papain by heat, the pH of the hydrolysates was adjusted to 7.0 and lyophilized.

Figure 9:
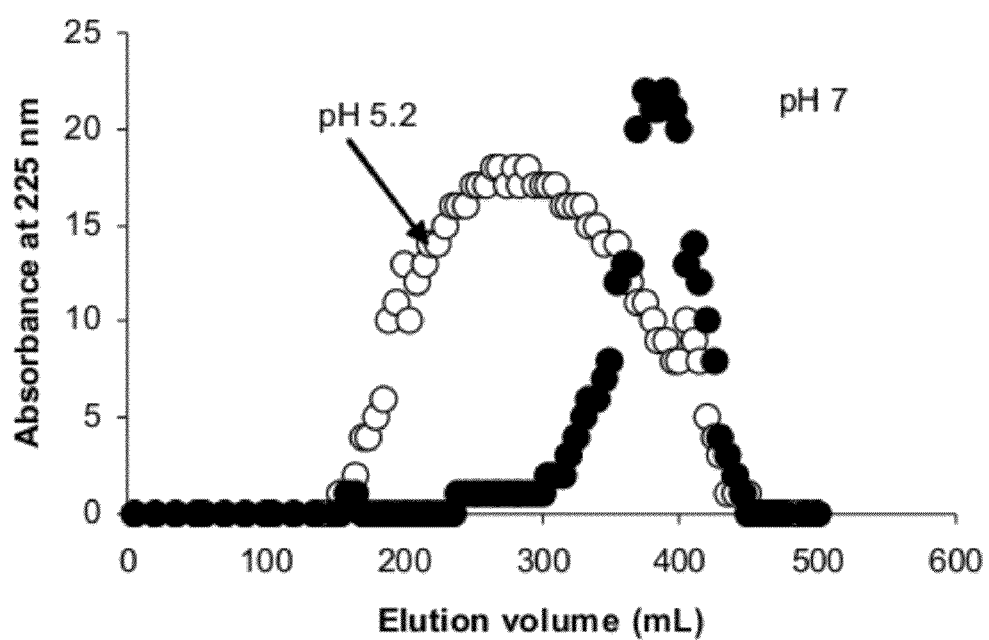
FIG. 9 is a graph showing the elution profile of gelatin hydrolysates produced at pH 5.2 and 7.0 with 20% gelatin (type 225B40) in water at a temperature of 37° C., hydrolysis time of 10 minutes, and a papain-to-gelatin ratio of 1:100.

FIG. 9 shows the elution profiles of the hydrolysates formed as described above on a Sephadex G-50 gel permeation column. As shown in FIG. 9, the pH 5.2 hydrolysate contained polypeptides with a broad molecular weight distribution ranging from about 3,300 to about 31,000 Da, with a maximum distribution of about 12,000 Da. By contrast, the pH 7 hydrolysate contained a narrow molecular weight distribution of polypeptides ranging from about 3300 to about 8900 Da, with a maximum distribution of about 5300 Da. The elution profile of pH 7 hydrolysate was similar to that of Fraction 3 in Example 1 (see FIG. 1).

Figure 10A:
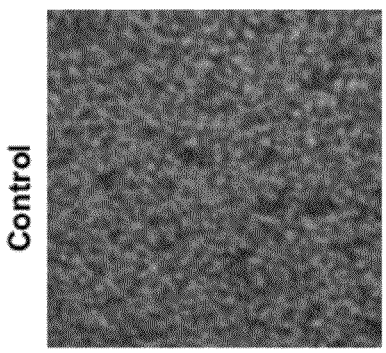
FIGS. 10A and 10B are microscopic images showing the effects of ice crystal growth in ice cream without gelatin hydrolysate before (FIG. 10A) and after (FIG. 10B) thermal cycling.
Figure 10B:
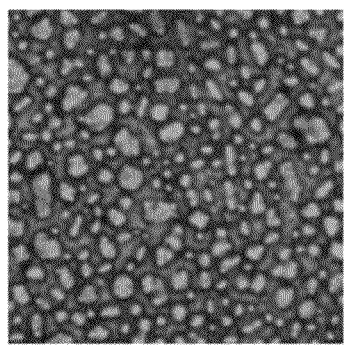
Figure 11A:
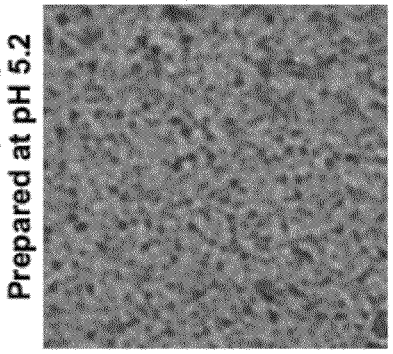
FIGS. 11A and 11B are microscopic images showing the effects of gelatin hydrolysate produced at pH 5.2 on ice crystal growth in ice cream before (FIG. 11A) and after (FIG. 11B) thermal cycling.
Figure 11B:
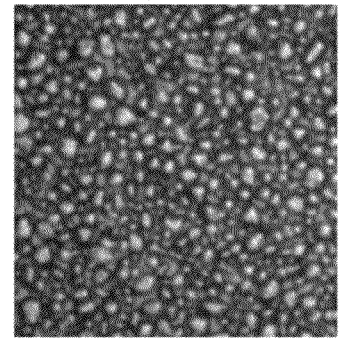
Figure 12A:
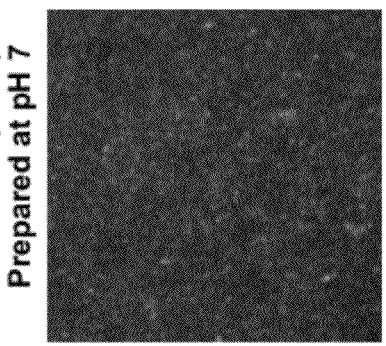
FIGS. 12A and 12B are microscopic images showing the effects of 0.5% gelatin hydrolysate produced at pH 7.0 on ice crystal growth in ice cream before (FIG. 12A) and after (FIG. 12B) thermal cycling.
Figure 12B:
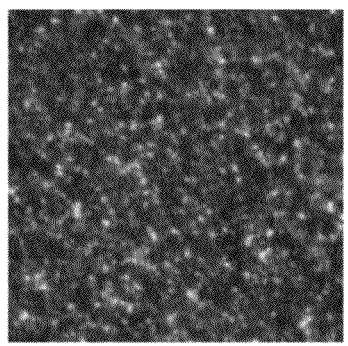

Ice crystal growth inhibition in ice cream by these hydrolysates is shown in FIGS. 10A through 13B. As shown in FIGS. 10A and 10B, the pH 5.2 hydrolysate did not exhibit significant inhibitory activity on ice crystal growth even at the 4% level after seven cycles at −14° C. to −12° C. Its behavior was very similar to that of Fractions 1 and 2 in Example 1 (see FIG. 1), presumably because it contained more of the high molecular weight peptides, similar to those found in Fractions 1 and 2, and less of the low molecular weight peptides, similar to Fraction 3, on a mass basis. By contrast, the pH 7.0 hydrolysate exhibited very remarkable inhibitory activity on ice crystal growth, even at 0.5 and 1.0 wt % levels and over 25 thermal cycles between about −14° C. and about −12° C. as shown in FIGS. 12A, 12B, 13A and 13B.

Example 3

In this example, gelatin hydrolysate was obtained by treating a 20 wt % gelatin in water at pH 7.0 with papain at various enzyme-to-substrate (E/S) weight ratios for 30 min at 37° C.

Figure 14:
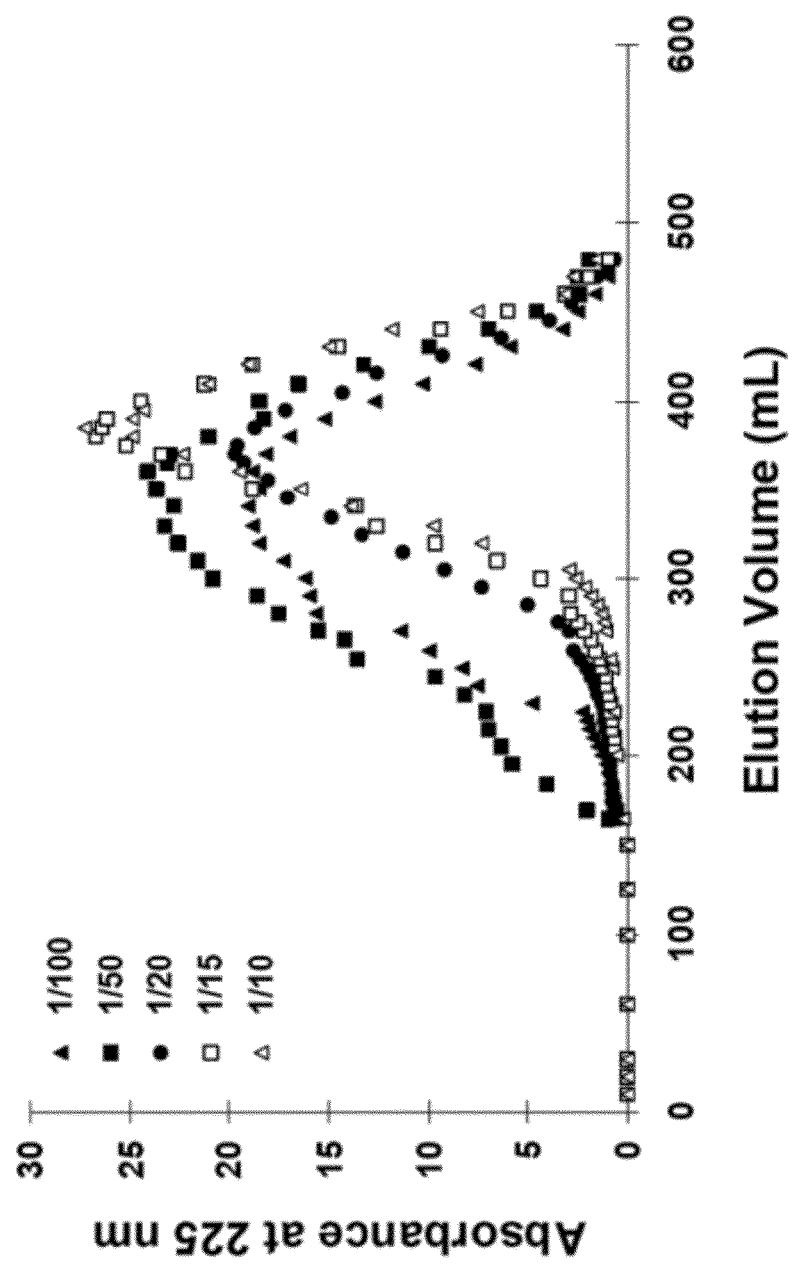
FIG. 14 is a graph showing the elution profile of gelatin hydrolysate on a Sephadex G-50 gel permeation column with the gelatin hydrolysate being produced by treating a 20 wt % gelatin in water at pH 7.0 with papain at various enzyme-to-substrate (E/S) weight ratios for 30 min at 37° C.
Figure 15:
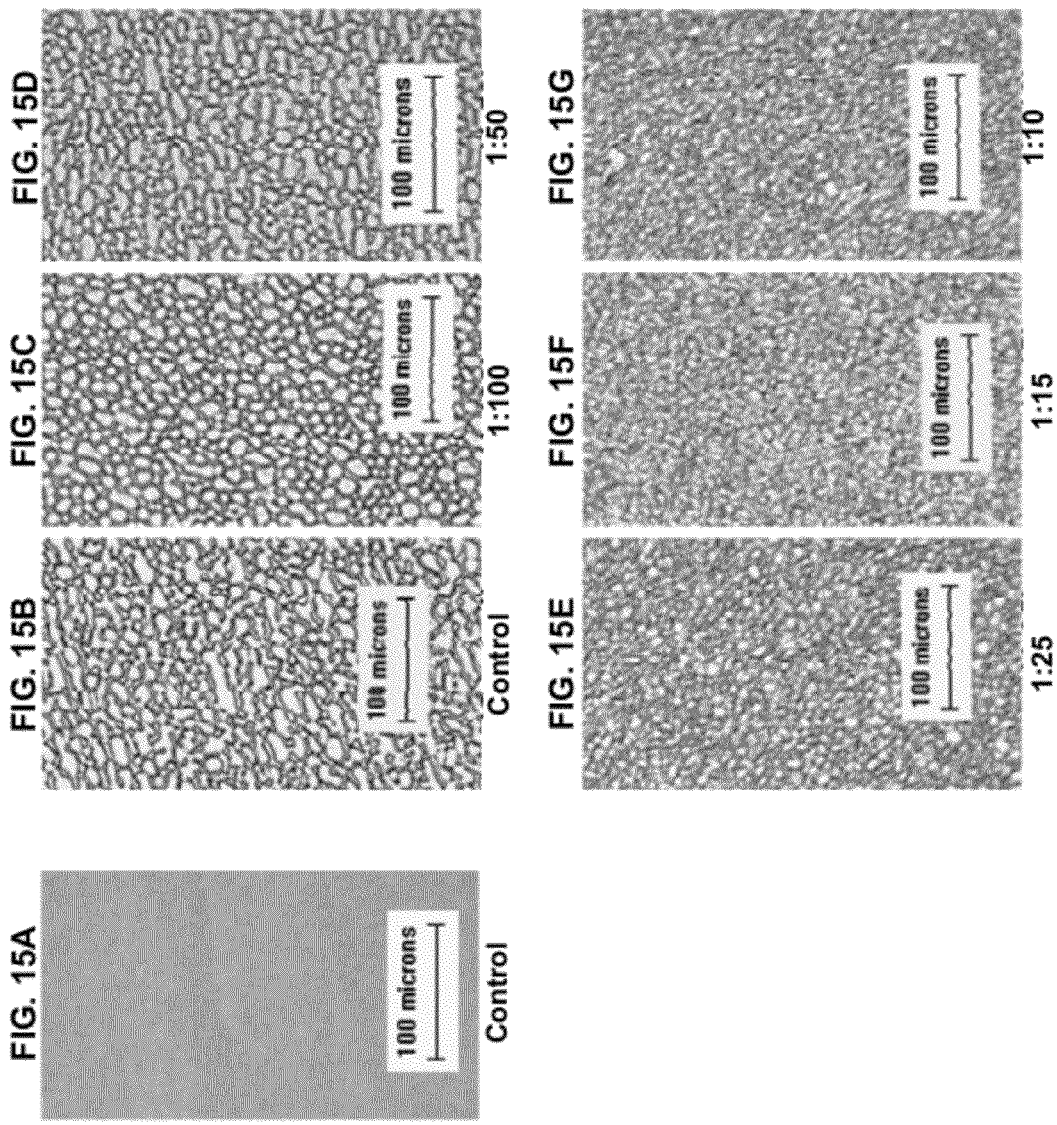
FIGS. 15A-15G are microscopic images showing the effects of 4% unfractionated gelatin produced as described for FIG. 14 at 1:100 (FIG. 15C), 1:50 (FIG. 15D), 1:25 (FIG. 15E), 1:15 (FIG. 15F), and 1:10 (FIG. 15G) enzyme-to-substrate ratios after thermal cycling.

FIG. 14 shows elution profiles of gelatin hydrolysate resulting from the various E/S ratios. The E/S ratio was in weight ratio of enzyme in liquid form (2.64 Anson units/g) to dry weight of gelatin. The elution profile of the hydrolysate on the Sephadex G-50 column shifted to the right as the E/S ratio was increased, indicating that the average molecular mass of peptides liberated in the hydrolysate decreased with increasing E/S ratio.

FIGS. 15A-G show the effects of the above gelatin hydrolysate (unfractionated) on ice crystal growth in the ice cream mix after seven thermal cycles between −14 and −12° C. at 4 wt % level. The hydrolysates obtained with an E/S ratio of 1:15 to 1:10 exhibited the maximum ice crystal growth inhibition activity.

Figure 16:
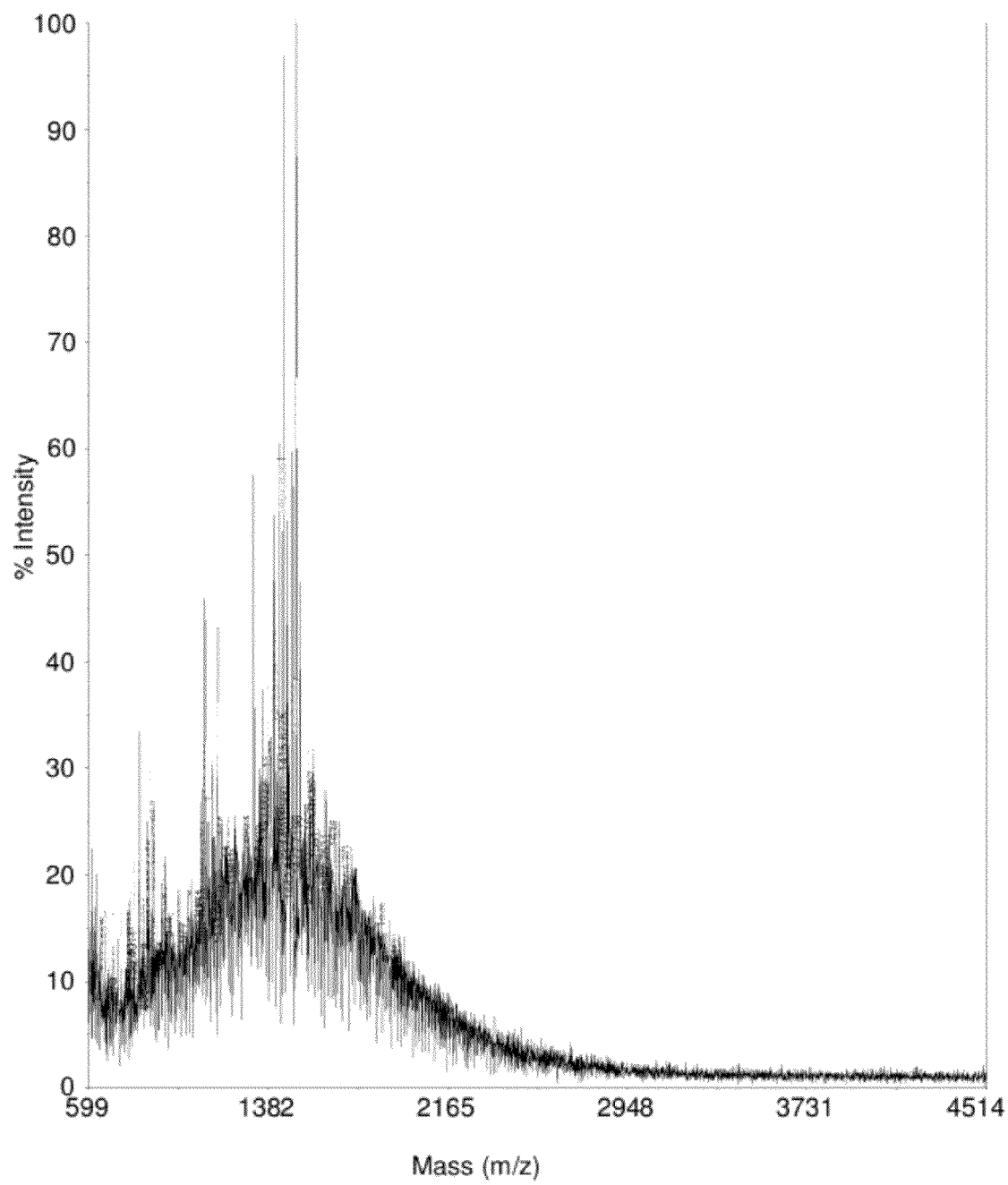
FIG. 16 is a matrix-assisted laser desorption-ionization-time of flight (MALDI-TOF) spectrum showing the molecular weight distribution of total gelatin hydrolysates produced at pH 7.0 at 37° C. for 30 minutes at a papain-to-gelatin ratio of 1:10.

FIG. 16 shows the MALDI-TOF molecular mass distribution of peptides in gelatin hydrolysate obtained with E/S ratio of 1:10.

To determine if peptides with a specific molecular weight range were responsible for the ice recrystallization inhibition activity, hydrolysate was produced using papain under optimal conditions (pH 7.0 at 37° C., E/S ratio of 1:10 and 30 min hydrolysis time), fractionated on a Sephadex G-50 gel filtration column, pooled into three major fractions based on molecular weight, and lyophilized. FIG. 17 shows the resulting elution profile and pooled fractions.

FIGS. 18A-D show the ice structuring activities of the three pooled fractions. Among the three fractions, Fraction 2 exhibited the highest ice crystal growth inhibition activity.

Table 1 shows the mean ice crystal size in ice cream mix treated with Fractions 1-3 in FIGS. 17 and 18A-D after thermal cycling.

TABLE 1

| Fraction | Diameter (±SD) μm |
| --- | --- |
| Control | 22.16 ± 1.21$^A$ |
| Total Gelatin Hydrolysate | 6.32 ± 0.34$^B$ |
| Fraction 1 of Sephadex G-50 | 19.68 ± 0.69$^A$ |
| Fraction 2 of Sephadex G-50 | 4.62 ± 0.26$^C$ |
| Fraction 3 of Sephadex G-50 | 7.63 ± 0.34$^D$ |

$^{A,B,C,D}$Values with the same superscript letters in the same column are not significantly different (P < 0.05).

As shown in Table 1, Fraction 2 produced the largest reduction in ice crystal size.

Figure 13A:
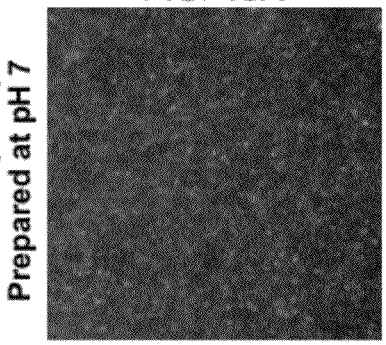
FIGS. 13A and 13B are microscopic images showing the effects of 1.0% gelatin hydrolysate produced at pH 7.0 on ice crystal growth in ice cream before (FIG. 13A) and after (FIG. 13B) thermal cycling.
Figure 13B:
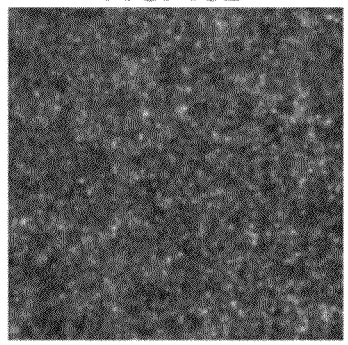
Figure 19:
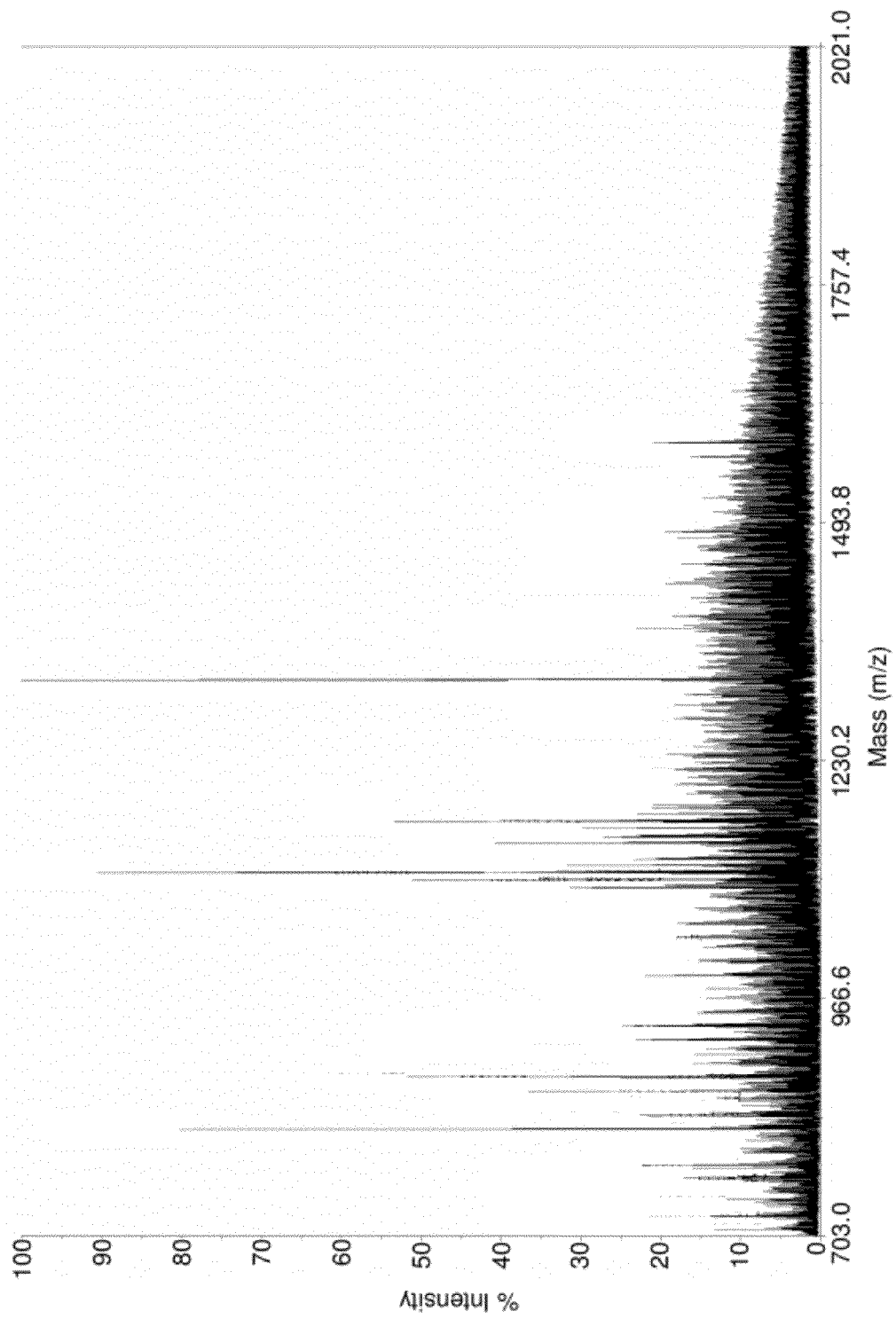
FIG. 19 shows a MALDI-TOF spectrum of Fraction 2 from FIG. 17.

FIG. 19 shows the MALDI-TOF mass spectrum of Fraction 2 from FIG. 13A. Peptides corresponding to molecular masses of 821.46 Da, 879.44 Da, 1037.57 Da, 1105.60 Da, 1162.57 Da, and 1318.72 Da were the dominant peptides in the mixture.

FIG. 20 shows cation exchange chromatography of Fraction 2 from FIG. 13A on Sulfopropyl-Sephadex C-25 (SP-Sephadex) using 0-0.5M NaCl gradient at pH 7.0. Two fractions were obtained, one corresponding to unadsorbed (anionic and neutral) peptides (SP1) that were eluted with 0 M NaCl and adsorbed (cationic) peptides (SP2) that were eluted by the 0-1.0 M NaCl gradient. The SP1 and SP2 fractions were pooled separately, exhaustively dialyzed using a 500 molecular weight cut-off (MWCO) membrane, and lyophilized.

FIGS. 21A-C show ice crystal growth inhibition in ice cream mix after seven cycles at −14 to −12° C. at 4 wt %. The cationic SP2 Fraction was more effective than the SP1 Fraction. These results indicate that, in addition to size distribution, the charge characteristics of gelatin peptides also play a critical role in recrystallization inhibition activity.

Figure 22:
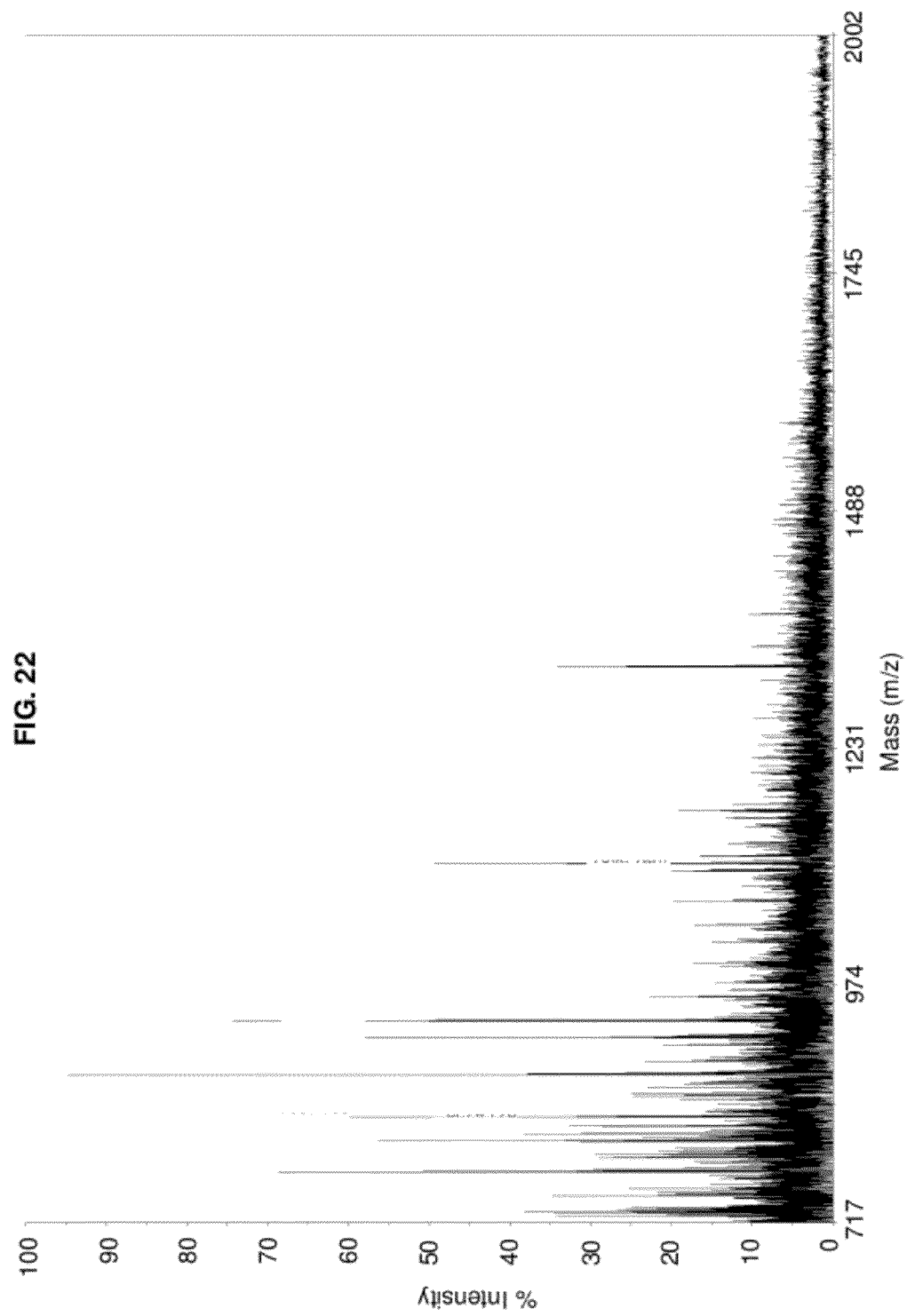
FIG. 22 shows a MALDI-TOF spectrum of the SP2 Fraction from FIG. 20.

FIG. 22 shows MALDI-TOF mass spectrum of the SP2 fraction. The molecular mass was in the range of 700 Da to 1400 Da.

Figure 23:
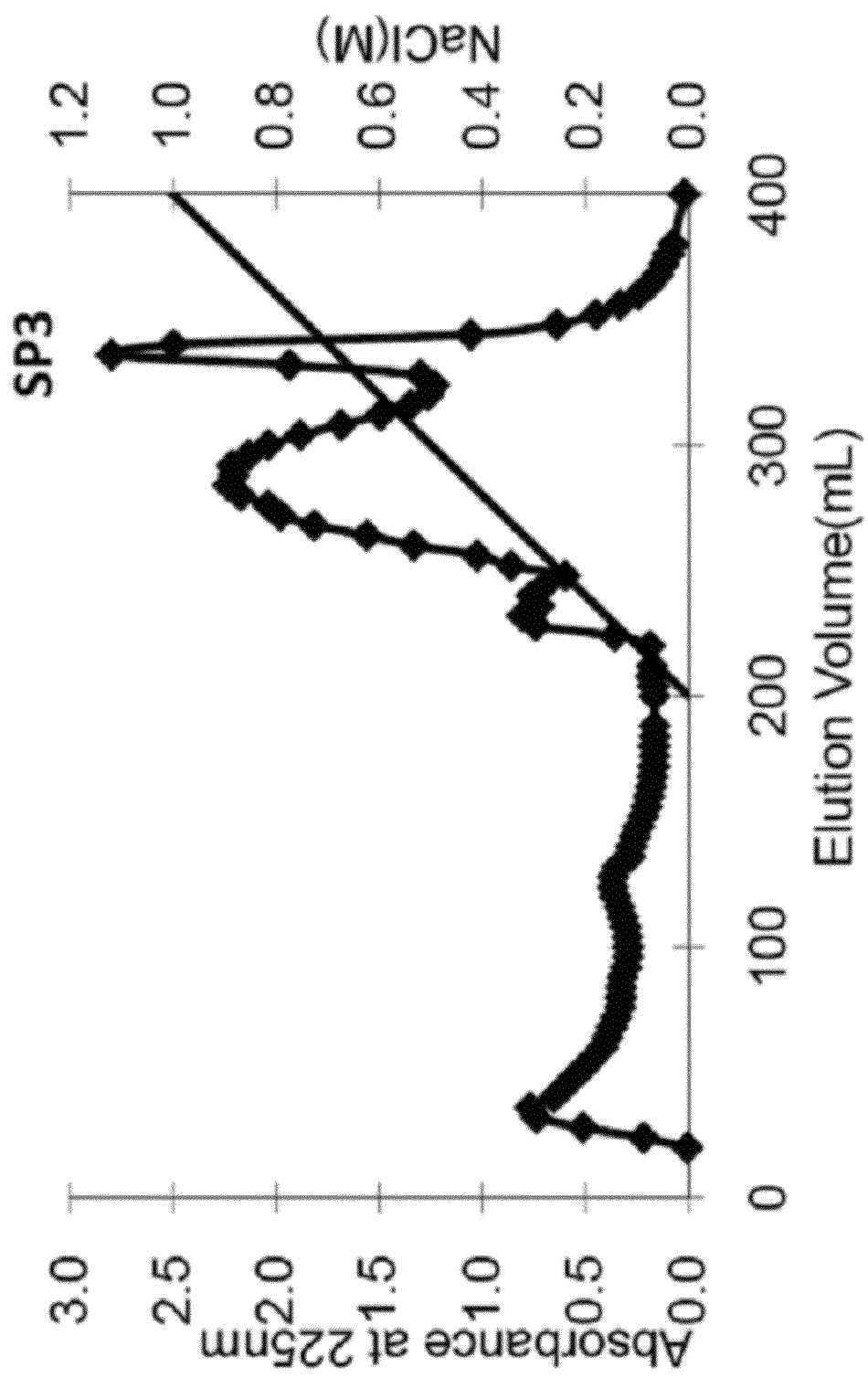
FIG. 23 is a graph showing the elution profile from cation exchange chromatography of Fraction 2 from FIG. 17 on an SP-Sephadex column using a 0-1 M NaCl gradient at pH 4.0.

FIG. 23 shows ion exchange chromatography of Fraction 2 from FIG. 13A on a Sulfopropyl-Sephadex C-25 (SP-Sephadex) column (2.0 cm diameter×55 cm length) using a 0-1.0 M NaCl gradient at pH 4.0. The tubes corresponding to the last elution peak (SP3) were pooled, exhaustively dialyzed using a 500 molecular weight cut-off (MWCO) membrane, and lyophilized.

Figure 24:
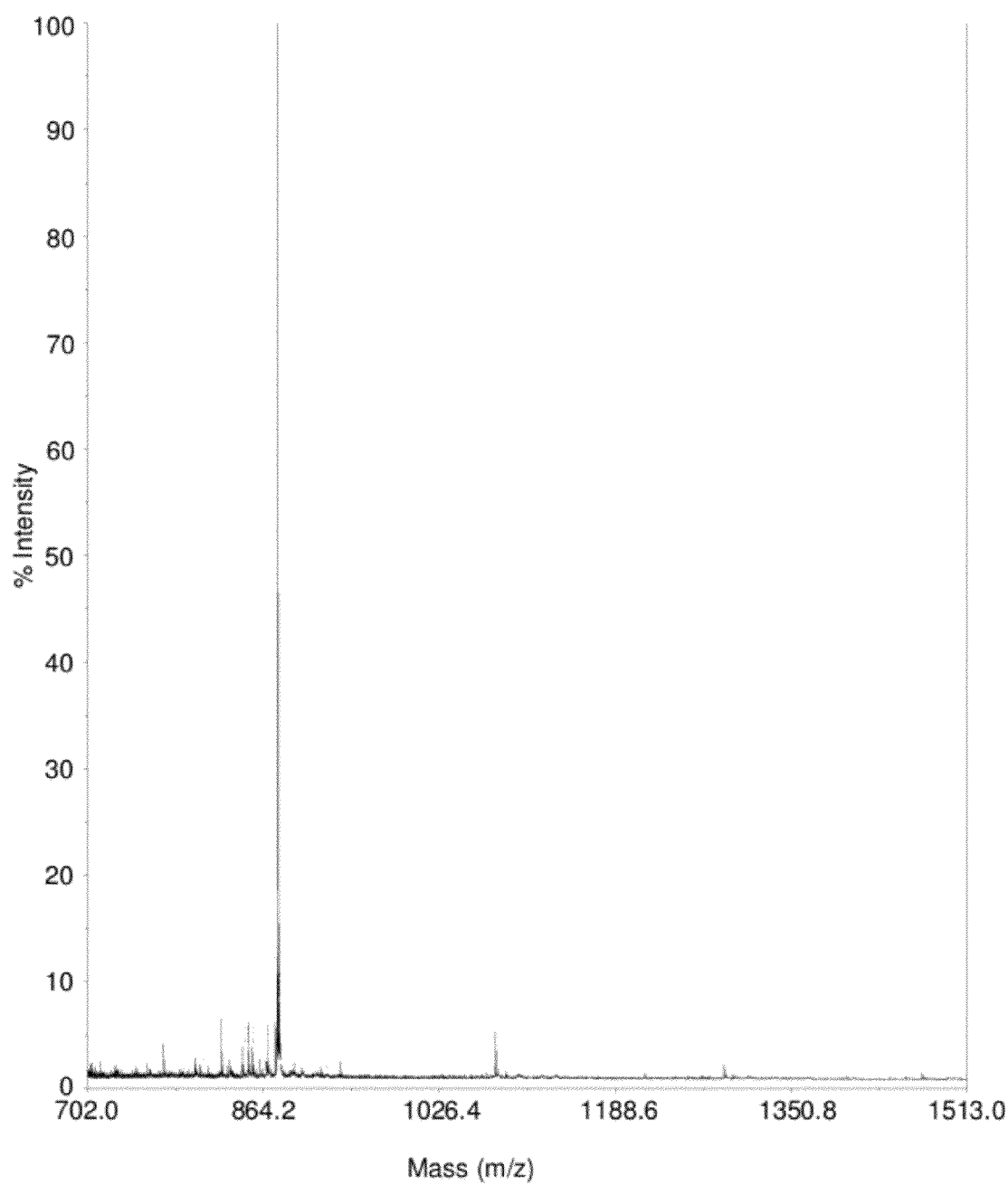
FIG. 24 is a MALDI-TOF mass spectrum of the SP3 fraction from FIG. 23.

FIG. 24 shows MALDI-TOF mass spectrum of the SP3 fraction. The molecular mass was in the range of 700 Da to 1400 Da. However, it contained only one dominant peak with a molecular mass of 877 Da.

FIGS. 25A-G show ice crystal growth inhibition activity of SP3 in ice cream mix after seven cycles at −14 to −12° C. at various concentration levels. SP3 showed activity even at 0.25%.

Example 4

In this example, gelatin hydrolysate was obtained by treating a 20 wt % gelatin in water at pH 9.0 with ALCALASE at various enzyme-to-substrate (E/S) weight ratios for 30 min at 45° C. The E/S ratio was in weight ratio of enzyme in liquid form (2.64 Anson units/g) to dry weight of gelatin.

Figure 26:
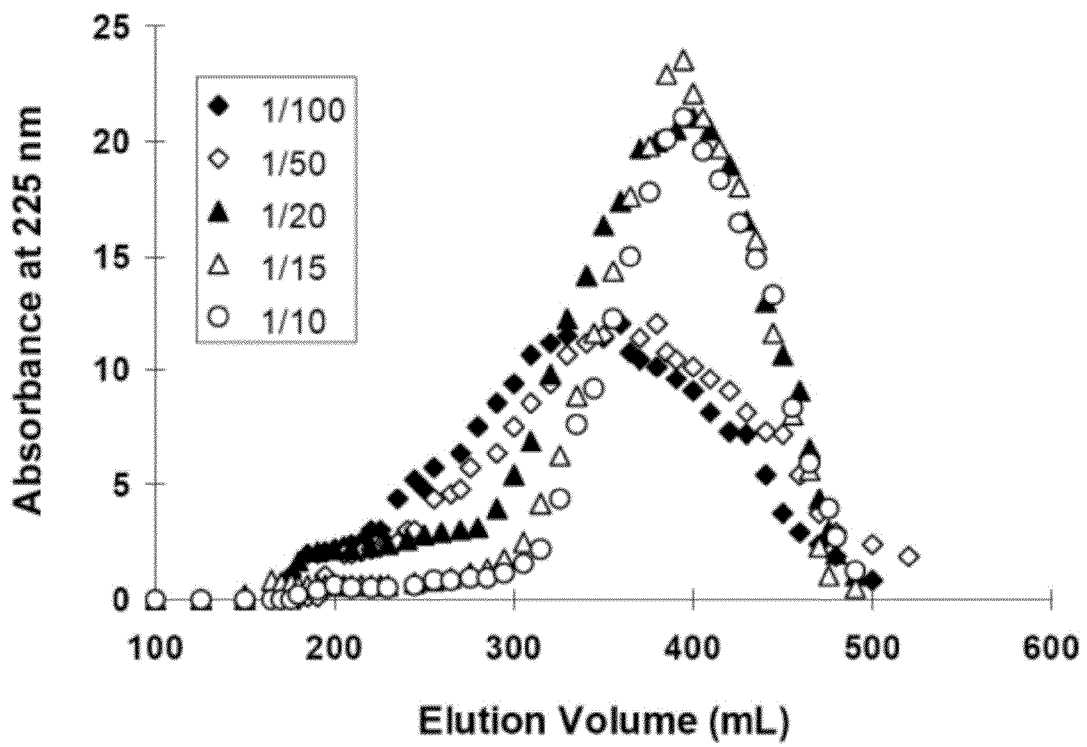
FIG. 26 is a graph showing the elution profile of gelatin hydrolysate on a Sephadex G-50 gel permeation column with the gelatin hydrolysate being produced by treating a 20 wt % gelatin in water at pH 9.0 with ALCALASE at various enzyme-to-substrate (E/S) weight ratios for 30 min at 45° C.

FIG. 26 shows elution profiles of the resulting gelatin hydrolysate. The elution profile of the hydrolysate on the Sephadex G-50 column shifted to the right as the E/S ratio was increased, indicating that the average molecular mass of peptides liberated in the hydrolysate decreased with increasing E/S ratio.

FIGS. 27A-G show the effects of total (i.e., unfractionated) gelatin hydrolysate on ice crystal growth in the ice cream mix after seven thermal cycles between −14 and −12° C. At 4 wt % level, the total gelatin hydrolysate obtained at an E/S ratio of 1:100 was not able to inhibit ice crystal growth during thermal cycling. At higher E/S ratios, ice crystal growth inhibition activity of the hydrolysate increased with increasing E/S ratio.

Figure 28:
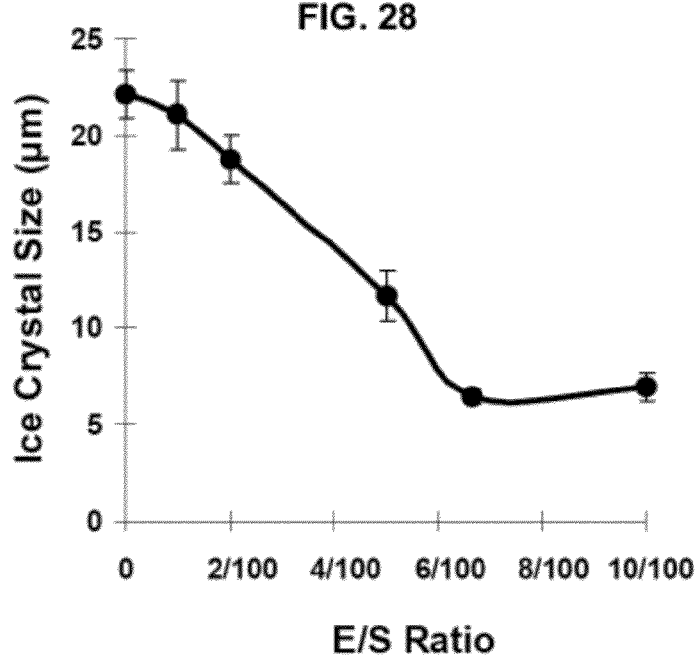
FIG. 28 is a graph showing the relationship between average ice crystal size versus the enzyme-to-substrate ratio used to produce gelatin hydrolysate as described for FIG. 26.

FIG. 28 shows the relationship between E/S ratio and the average size of ice crystals formed after seven thermal cycles. The hydrolysate obtained using an E/S ratio of 1:15 was to be the most active in terms of reducing the average size of ice crystals.

Figure 29:
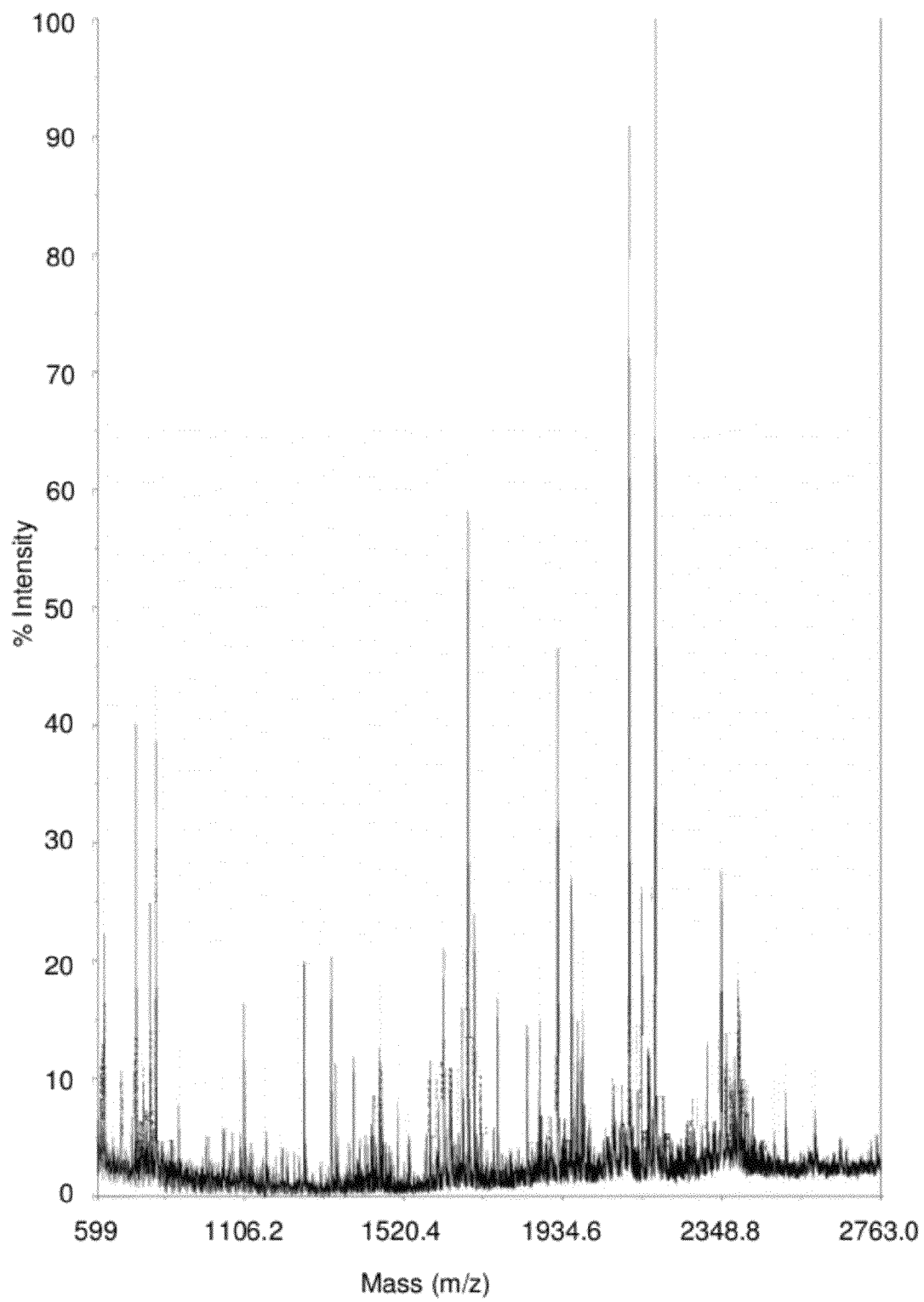
FIG. 29 is a MALDI-TOF mass spectrum of crude hydrolysate obtained with an enzyme-to-substrate ratio of ALCALASE of 1:15 as described for FIG. 26.

FIG. 29 shows the MALDI-TOF mass spectrum of the peptides in the hydrolysate produced using an E/S ratio of 1:15 under the above conditions. The molecular weight of the peptides in the hydrolysate was in the range of 600-2800 Da.

To elucidate which of the peptides within the molecular mass range 600-2800 Da were greatly responsible for the ice recrystallization inhibition activity, the gelatin hydrolysate was produced under optimal conditions (pH 9.0 at 45° C., E/S ratio of 1:15 and 30 min hydrolysis time), fractionated on Sephadex G-50 gel filtration column, pooled into three major fractions, and lyophilized. FIG. 30 shows the resulting elution profile and pooled fractions.

FIGS. 31A-D show the ice structuring activities of the three pooled fractions. Fraction 2 (from the middle portion of the elution profile) exhibited the highest activity with an average ice crystal size of 5.02±0.55 µm. Although the ice structuring activity of Fraction 3 (8.39±0.58 µm) was statistically poorer than Fraction 2, it was significantly better than Fraction 1 (17.96±1.13 µm) and the control (22.16±1.21 µm).

Figure 32:
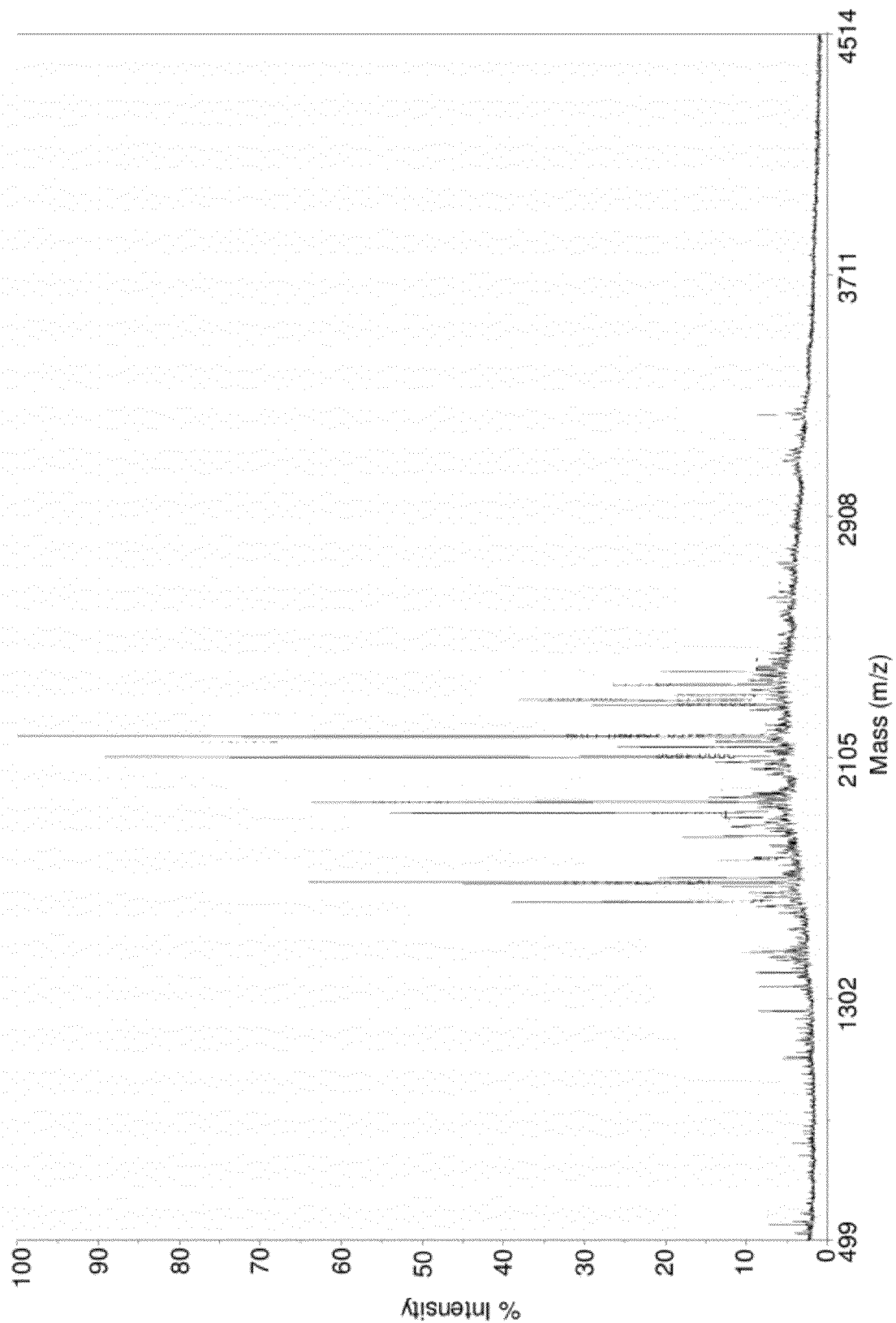
FIG. 32 shows a MALDI-TOF spectrum of Fraction 2 from FIG. 30.

FIG. 32 shows the MALDI-TOF mass spectrum of Fraction 2. Although Fraction 2 contained several peptides, those corresponding to molecular masses of 1625.40 Da, 1672.86 Da, 1688.84 Da, 1921.02 Da, 1957.09 Da, 2107.09 Da, and 2175.10 Da, 2280.15 Da and 2296.14 Da were the dominant peptides in the mixture. The relative intensity of these peptides in different batches of Fraction 2 was very similar, suggesting that although ALCALASE is essentially a non-specific enzyme, its cleaving pattern is basically the same as long as the hydrolysis condition is kept the same.

Figure 33:
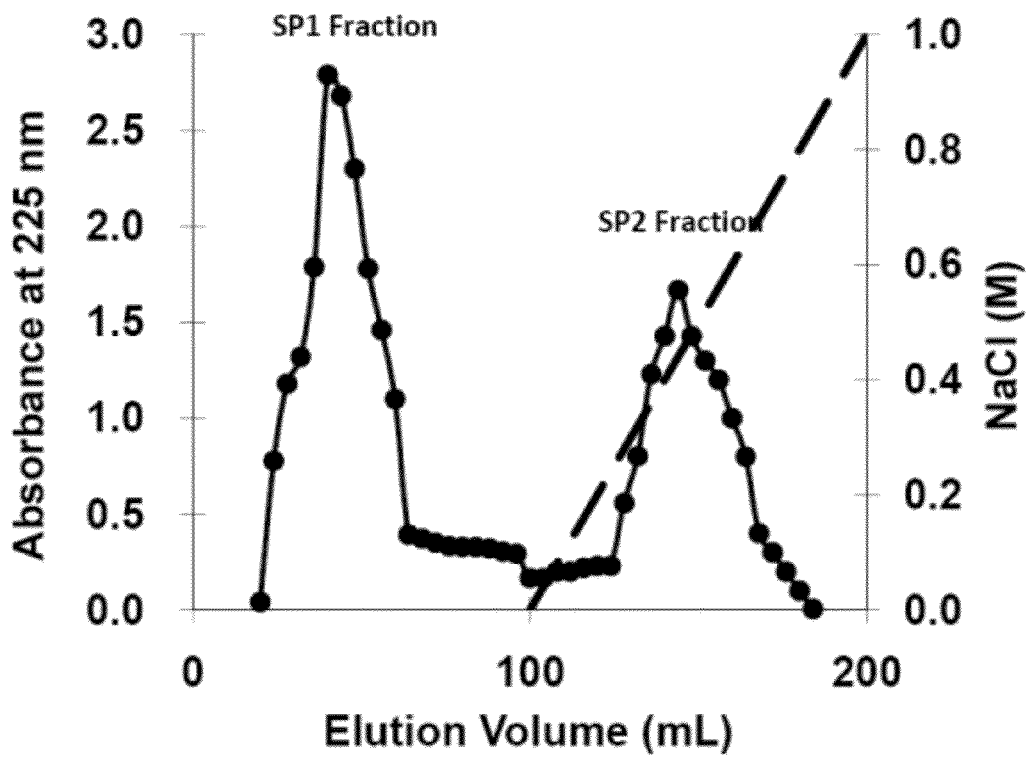
FIG. 33 is a graph showing the elution profile from ion exchange chromatography of Fraction 2 from FIG. 30 on SP-Sephadex using a 0-1.0 M NaCl gradient at pH 7.0.

FIG. 33 shows ion exchange chromatography of Fraction 2 on a Sulfopropyl-Sephadex C-25 (SP-Sephadex) column (2.0 cm diameter×55 cm length) using a 0-1.0 M NaCl gradient in 0.01 M phosphate buffer, pH 7.0. Two fractions were obtained, one corresponding to unadsorbed (anionic and neutral) peptides (SP1) that were eluted with 0 M NaCl and adsorbed (cationic) peptides (SP2) that were eluted by the 0-1.0 M NaCl gradient. The SP1 and SP2 fractions were pooled separately, exhaustively dialyzed using a 500 molecular weight cut-off (MWCO) membrane, and lyophilized.

Figure 34A:
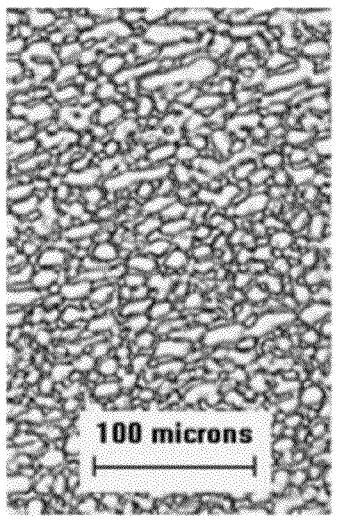
FIGS. 34A-34C are microscopic images showing the effect of no gelatin hydrolysate (FIG. 34A) and the SP1 (FIG. 34B) and SP2 (FIG. 34C) Fractions from FIG. 33 on ice crystal growth in ice cream after thermal cycling.
Figure 34B:
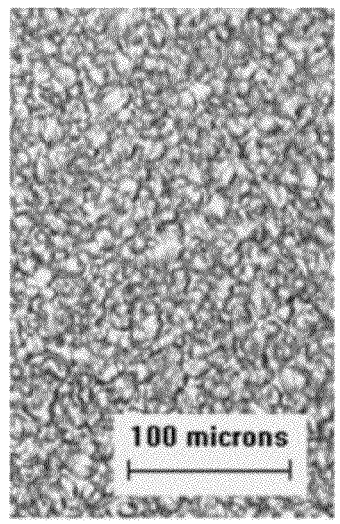
Figure 34C:
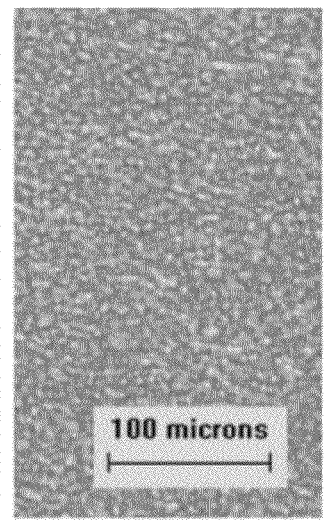

FIGS. 34A-C show the ice recrystallization inhibition activity of SP1 and SP2 Fractions. The SP2 Fraction (cationic peptides) was more effective than the SP1 Fraction in inhibiting ice recrystallization. The average size of ice crystals was about 3.35±0.46 µm in the SP2 Fractin-containing sample, 9.16±0.89 µm in the SP1 Fraction-containing sample, and 22.16±1.21 µm in the control. The SP2 fraction was able to significantly retard ice crystal growth even after 25 thermal cycles between −12 and −14° C. These results further indicate that, in addition to size distribution, the charge characteristics of gelatin peptides also play a critical role in recrystallization inhibition activity.

Figure 35:
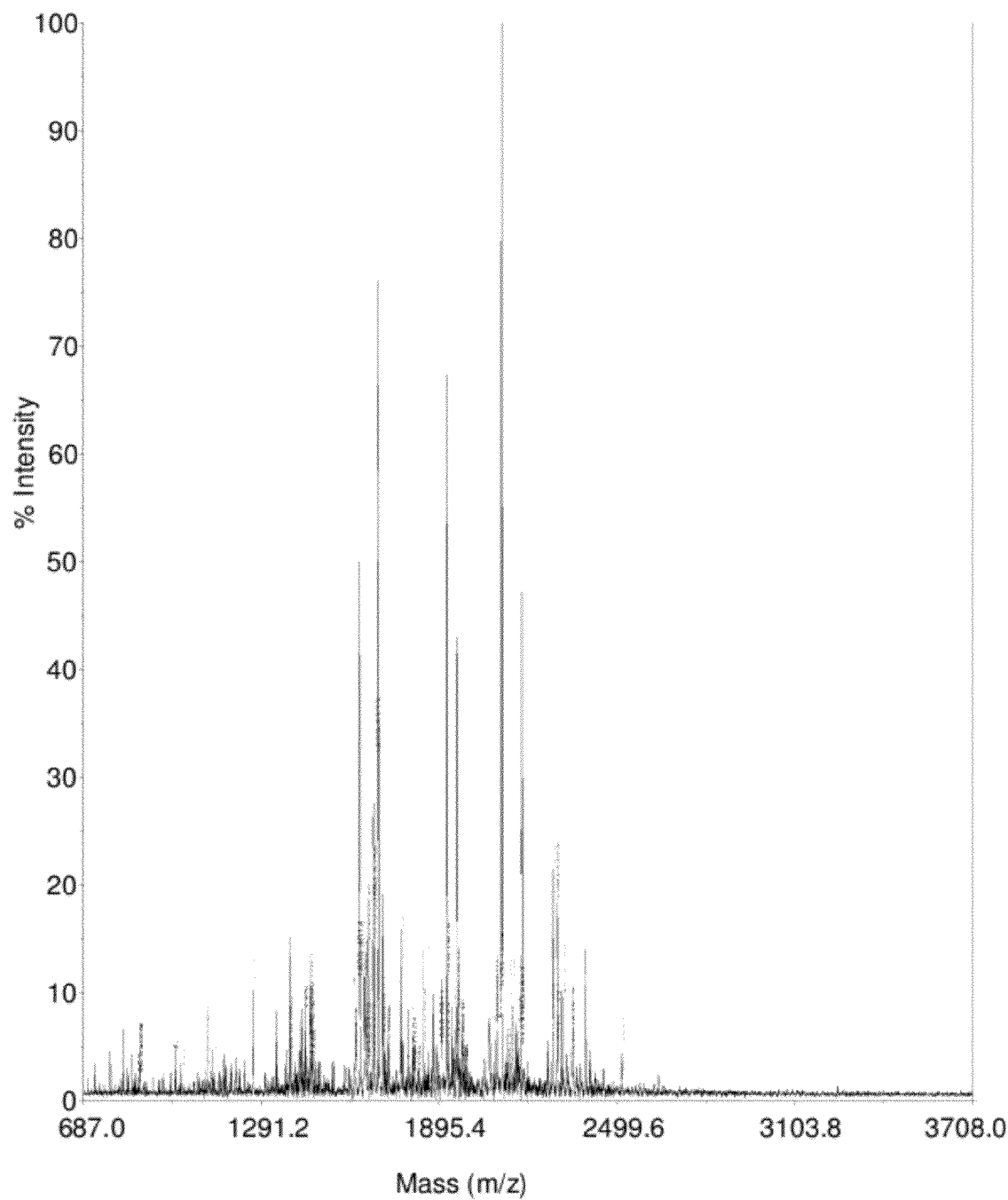
FIG. 35 shows a MALDI-TOF spectrum of the SP2 Fraction from FIG. 33.

FIG. 35 shows the MALDI-TOF mass spectrum of the SP2 fraction. The cationic SP2 fraction contained about 6 major peptides with m/z values 1625.39, 1688.83, 1921.00, 1957.07, 2107.07, and 2176.08 Da. The peptide with a mass of 2107.07 Da was dominant among these peptides.

Figure 36:
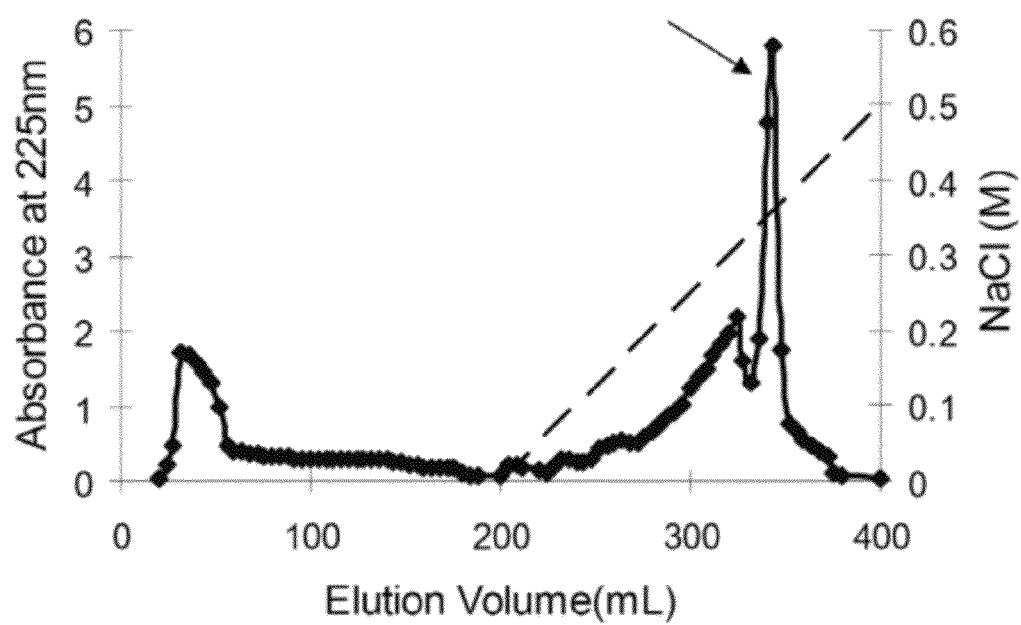
FIG. 36 is a graph showing the elution profile from cation exchange chromatography of Fraction 2 from FIG. 30 on an SP-Sephadex column using a 0-0.5 M NaCl gradient at pH 4.0.

FIG. 36 shows ion exchange chromatography of Fraction 2 on a Sulfopropyl-Sephadex C-25 (SP-Sephadex) column (2.0 cm diameter×55 cm length) using a 0-0.5 M NaCl gradient at pH 4.0. The tubes corresponding to the last elution peak indicated by an arrow were pooled separately, exhaustively dialyzed using a 500 molecular weight cut-off (MWCO) membrane, and lyophilized.

Figure 37:
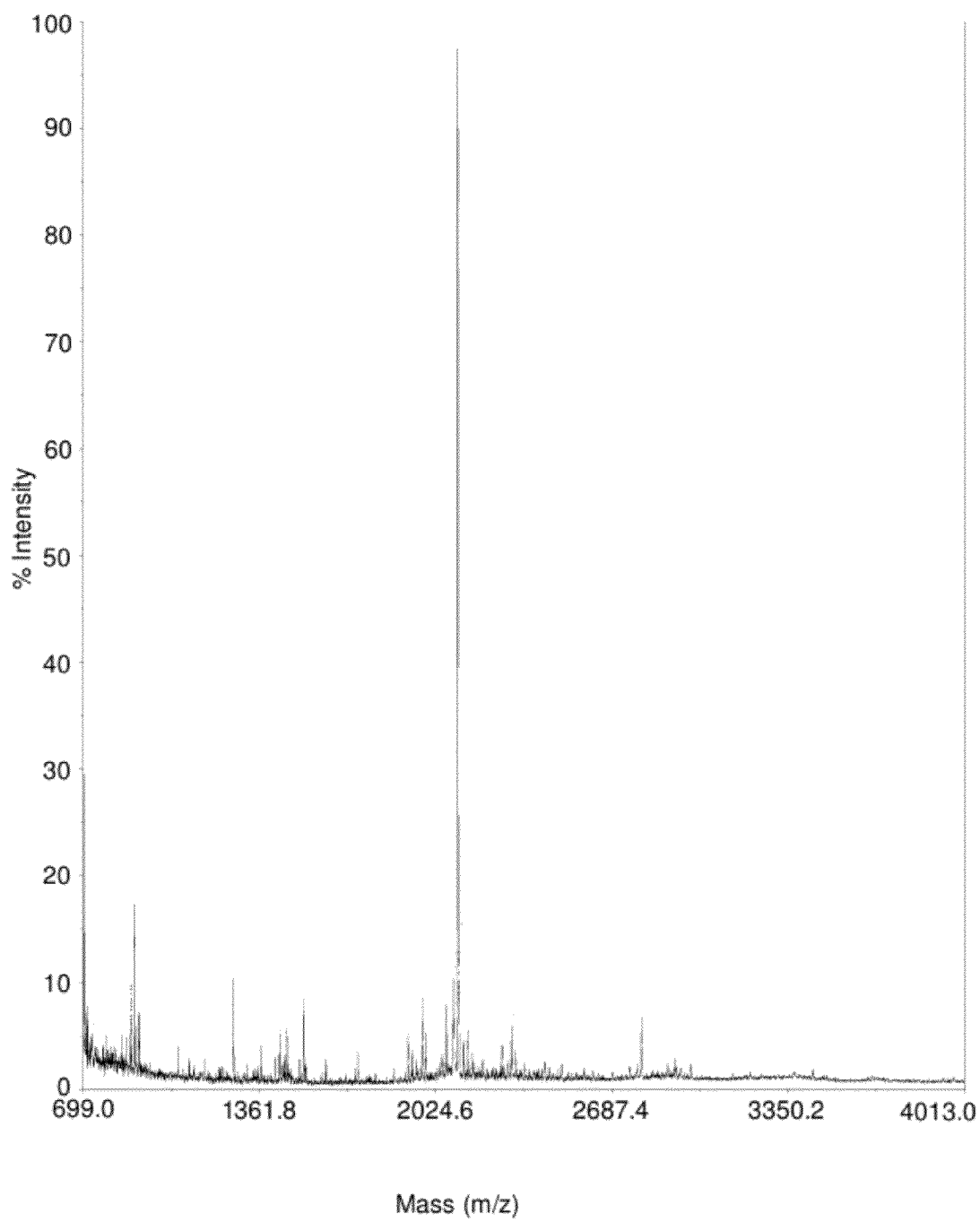
FIG. 37 is a MALDI-TOF mass spectrum of the eluate from the peak indicated by the arrow in FIG. 36.
Figure 39:
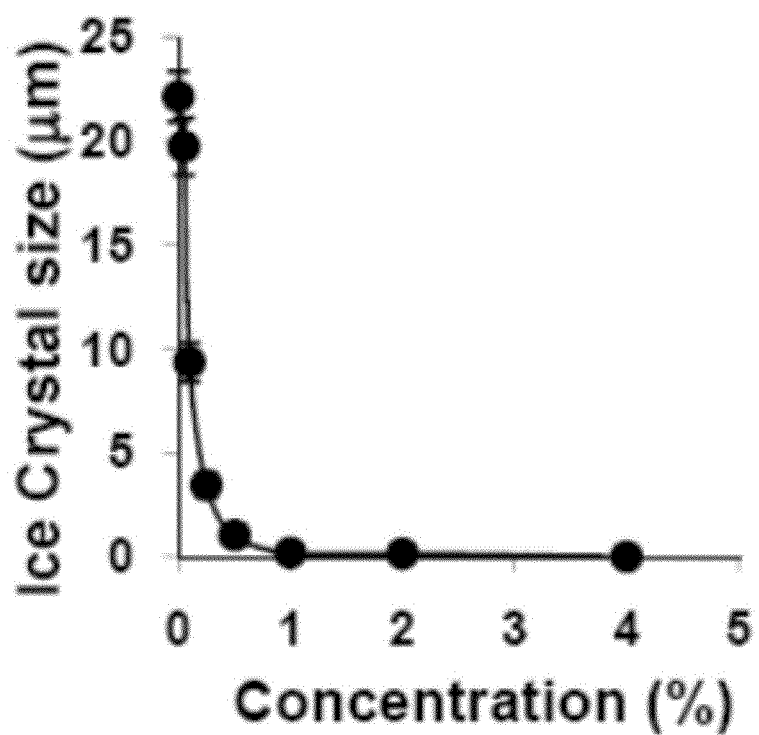
FIG. 39 is a graph showing the average ice crystal size versus concentration of the 2107 Da gelatin peptide from FIG. 37 in ice cream mix after thermal cycling.

FIG. 37 shows MALDI-TOF of the above fraction. This fraction essentially contained a single peptide having a molecular mass of 2107 Da. The amino acid sequence of this peptide, as determined by the Edman degradation method, was: Gly-Glu-Arg-Gly-Phe-Hyp-Gly-Glu-Arg-Gly-Val-Glu-Gly-Pro-Hyp-Gly-Pro-Ala-Gly-Pro-Arg (SEQ ID NO: 1).

FIGS. 38A-H and 39 show ice recrystallization inhibition activity of the 2107 Da peptide in ice cream mix at different concentrations. The 2107 Da peptide was very effective even at 0.1% concentration and at 1.0% there was essentially no ice crystal growth.

Example 5

Gelatin is a very unique protein. On an average, it contains 33% Gly, 33% Pro (and hydroxyproline (Hyp)), and the remaining other amino acid residues. Generally, the amino acid sequence of gelatin is often depicted as -(Gly-Pro(Hyp)-X)$_n$-, where X is any amino acid residue. However, in the primary structure of collagen, where the first position of this tripeptide repeat is always occupied by Gly, the second position is not always occupied by Pro or Hyp. In addition to -Gly-Pro(Hyp)-X- segments, there are several segments with sequences -Gly-Z-X- (where Z is any amino acid residue) within the collagen sequence. Thus, -Gly-Pro(Hyp)-X- and -Gly-Z-X- would be the major repeating units in the peptide fragments of the hydrolysate.

Common features among known antifreeze proteins is that their ice binding face is flat and that the distance between oxygen atoms on this face is about the same as that in ice nuclei, that is, about 4.52 Å (Hew et al., *Eur. J. Biochem.* 203:33-42 (1992) and Yang et al., *Biophys. J.* 74:2142-2151 (1998)). To examine whether the Gly-Pro(Hyp)-X- and Gly-Z-X segments in small peptides of gelatin hydrolysate adopt a flat face with the oxygen atoms of the carbonyl groups geometrically aligned with the oxygen-oxygen distance in ice nuclei, several model gelatin peptides were analyzed using ChemSite Pro Molecular Modeling software. We selected model gelatin peptides of the type Gly-Pro-X-Gly-Pro-Z-Gly (SEQ ID NO: 3) for the structural analysis. The rationale for selecting these model peptides was as follows; glycine residues occur at every third residue in the primary sequence of gelatin. Because papain and ALCALASE are nonspecific endoproteases, it is reasonable to assume that there is a 33% probability of having glycine at the C-terminus of peptides in gelatin hydrolysate. Furthermore, papain prefers a bulky hydrophobic residue at the P2 position (Berger et al., *Phil. Trans. Roy. Soc. Lond. B* 257:249-264 (1970)), and therefore, the presence of a bulky chain at the X position of the -Gly-Pro(Hyp)-X-tripeptide repeat also would result in liberation of peptides predominantly with -Gly-Pro(Hyp)-X-Gly (residues 1-4 of SEQ ID NO: 3) as the C-terminal segment.

In the energy-minimized structure of the peptide Gly-Pro-Pro-Gly-Pro-Ala-Gly (SEQ ID NO: 5), the oxygen atoms O[38] (C-terminal carbonyl group), O[34] (carbonyl group of Ala residue), and O[27] (carbonyl group of Pro residue) lie on a flat face. In this configuration, the distance between O[34] and O[38] is 4.538 Å, and that between O[34] and O[27] is 4.552 Å. These distances are very close to the 4.52 Å found in the prism face of ice nuclei. This region of the molecule is highly hydrophilic, and no other discernible oxygen grouping is apparent in the molecule.

Extension of the peptide chain length of the gelatin model peptide by one repeat unit does not significantly change the configuration of this flat face. The molecule essentially assumes a collagen-type helix structure as the chain length is increased. The configuration of the oxygen-containing flat face of the energy-minimized structure of Gly-Pro-Pro-Gly-Pro-Ala-Gly-Pro-Ala-Gly (SEQ ID NO: 7) is essentially the same as that of Gly-Pro-Pro-Gly-Pro-Ala-Gly (SEQ ID NO: 5), and no other hydrophilic region with O-O distance and configuration similar to that of ice nuclei is found on other parts of the molecule. We hypothesize that these three oxygen atoms, which lie on a plane, constitute the ice binding face of these gelatin peptides.

Variations in amino acid residues at the X and Z positions may, however, affect the configuration of the ice binding face. For instance, the energy-minimized structure of Gly-Pro-Thr-Gly-Pro-Leu-Gly (SEQ ID NO: 9) displays three oxygen atoms in a plane, but the O-O distances are 4.670 and 4.349 Å, both of which are not very compatible with the O-O distance in ice nuclei. By contrast, the energy-minimized structure of Gly-Pro-Hyp-Gly-Pro-Ala-Gly (SEQ ID NO: 5 with a hydroxylated proline at position 3) exhibits an oxygen plane with O-O distances of 4.565 and 4.542 Å, which are about the same as for Gly-Pro-Pro-Gly-Pro-Ala-Gly (SEQ ID NO: 5 without hydroxylated prolines) and O-O distances in ice nuclei. Thus, substitution of Hyp for Pro does not change the conformational characteristics and, hence, the antifreeze properties of the polypeptides.

Analyses of the energy-minimized structures of various model gelatin peptides suggested that sequences with small amino acid residues, such as Ala, Ser, Thr, Pro, Hyp, and Gly at X and Z positions invariably exhibited an oxygen triad plane (flat face) at the C-terminus with two O-O distances of close to 4.52 Å. Because no other hydrophilic surface with O-O configurations similar to that of ice nuclei is apparent in other parts of the molecule, we conclude that the oxygen triad plane is the ice binding region of the molecule. Several of these flat-faced peptides may bind to the prism face of ice nuclei via hydrogen bonding, thereby inhibiting their growth. The aliphatic side chains of proline and alanine residues may provide a partial nonpolar environment to stabilize such hydrogen bonding interactions against competition from ice-water hydrogen bonding interactions.

Gelatin peptides with molecular weights in the preferred ranges may be able to form stiff collagen-type helix rods, which may favor stacking of these rods on ice nuclei with the oxygen triad plane facing the prism face of ice nuclei. On the other hand, gelatin peptides greater than the preferred ranges may loosen their stiffness. As a result, steric hindrances may prevent proper stacking of the peptides on the prism face of ice nuclei, thus decreasing their ability to inhibit ice crystal growth.

In this specification, the word "about" is often used in connection with numerical values to indicate that mathematical precision of such values is not intended. Accordingly, it is intended that where "about" is used with a numerical value, a tolerance of ±5% is contemplated for that numerical value.

Any embodiment of any method or composition of the invention may be used with any other method or composition of the invention.

All combinations of method or process steps as used herein can be performed in any order, unless otherwise specified or clearly implied to the contrary by the context in which the referenced combination is made.

As used in this specification and the appended claims, the singular forms "a," "an," and "the" include plural referents unless the content clearly dictates otherwise. Thus, for example, reference to a composition containing "a polynucleotide" includes a mixture of two or more polynucleotides. The term "or" is generally employed in its sense including "and/or" unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All publications, patents and patent applications are herein expressly incorporated by reference to the same extent as if each individual publication or patent application was specifically and individually indicated by reference. In case of conflict between the present disclosure and the incorporated patents, publications, and references, the present disclosure should control.

The methods, compounds, and compositions of the present invention can comprise, consist of, or consist essentially of the essential elements and limitations described herein, as well as any additional or optional steps, ingredients, components, or limitations described herein or otherwise useful in biochemistry, enzymology and/or genetic engineering.

It is understood that the invention is not confined to the particular construction and arrangement of parts herein illustrated and described, but embraces such modified forms thereof as come within the scope of the following claims.

What is claimed is:

1. An antifreeze composition comprising a food product that includes a polypeptide consisting essentially of repeating units of sequence Gly-Z-X, wherein Z and X are any amino acid residue and the polypeptide is between about 500-7000 Da.

2. The antifreeze composition of claim 1 wherein Z and X are selected from the group consisting of Ala, Ser, Thr, Pro, Hyp, and Gly.

3. The antifreeze composition of claim 1 wherein the polypeptide comprises at least five contiguous residues of SEQ ID NO: 1.

4. The antifreeze composition of claim 1 wherein the polypeptide comprises a sequence selected from the group consisting of SEQ ID NO: 1, a variant thereof, and a fragment thereof, wherein the variant includes conservative substitutions of residues other than glycine.

5. The antifreeze composition of claim 4 wherein the variant is at least about 80% identical to SEQ ID NO: 1.

6. The antifreeze composition of claim 1 wherein the polypeptide comprises a sequence selected from the group consisting of SEQ ID NO: 3, SEQ ID NO: 5, SEQ ID NO: 7, fragments thereof, and repeating units thereof.

7. The antifreeze composition of claim 1 wherein the polypeptide is between about 600-2800 Da.

8. The antifreeze composition of claim 1 wherein the polypeptide is cationic.

9. A method of inhibiting ice crystal growth comprising adding to a composition to be frozen a polypeptide consisting essentially of repeating units of sequence Gly-Z-X, wherein Z and X are any amino acid residue and the polypeptide is between about 500-7000 Da.

10. The method of claim 9 wherein Z and X in the added polypeptide are selected from the group consisting of Ala, Ser, Thr, Pro, Hyp, and Gly.

11. The method of claim 9 wherein the added polypeptide comprises at least five contiguous residues of SEQ ID NO: 1.

12. The method of claim 9 wherein the added polypeptide comprises a sequence selected from the group consisting of SEQ ID NO: 1, a variant thereof, and a fragment thereof, wherein the variant includes conservative substitutions of residues other than glycine.

13. The method of claim 12 wherein the added polypeptide is at least about 80% identical to SEQ ID NO: 1.

14. The method of claim 9 wherein the added polypeptide comprises a sequence selected from the group consisting of SEQ ID NO: 3, SEQ ID NO: 5, SEQ ID NO: 7, fragments thereof, and repeating units thereof.

15. The method of claim 9 wherein the added polypeptide is between about 600-2800 Da.

16. The method of claim 9 wherein the added polypeptide is cationic.

17. The method of claim 9 wherein the composition is a food product.

18. The method of claim 17 wherein the food product is selected from the group consisting of ice cream, dough, frozen desserts, frozen pizza, fruits, and vegetables.

19. The method of claim 9 wherein the polypeptide is added in an amount of at least about 0.1%.

20. An antifreeze composition comprising a food product that includes a polypeptide consisting of repeating units of sequence Gly-Z-X that terminate in a sequence selected from the group consisting of Gly-Z-X and fragments thereof, wherein Z and X are any amino acid residue and the polypeptide is between about 500-7000 Da.

21. The antifreeze composition of claim 20 wherein Z and X are selected from the group consisting of Ala, Ser, Thr, Pro, Hyp, and Gly.

22. The antifreeze composition of claim 20 wherein the polypeptide comprises at least five contiguous residues of SEQ ID NO: 1.

23. The antifreeze composition of claim 20 having a sequence selected from the group consisting of SEQ ID NO: 1, a variant thereof, and a fragment thereof, wherein the variant includes conservative substitutions of residues other than glycine.

24. The antifreeze composition of claim 23 wherein the variant is at least about 80% identical to SEQ ID NO: 1.

25. The antifreeze composition of claim 20 wherein the polypeptide comprises a sequence selected from the group consisting of SEQ ID NO: 3, SEQ ID NO: 5, SEQ ID NO: 7, and fragments thereof.

26. The antifreeze composition of claim 20 wherein the polypeptide is between about 600-2800 Da.

27. The antifreeze composition of claim 20 wherein the polypeptide is cationic.

28. The antifreeze composition of claim 20 wherein polypeptide consists entirely of repeating units of the sequence Gly-Z-X.

29. A method of inhibiting ice crystal growth comprising adding to a composition to be frozen a polypeptide consisting of repeating units of sequence Gly-Z-X that terminate in a sequence selected from the group consisting of Gly-Z-X and fragments thereof, wherein Z and X are any amino acid residue and the polypeptide is between about 500-7000 Da.

30. The method of claim 29 wherein Z and X in the added polypeptide are selected from the group consisting of Ala, Ser, Thr, Pro, Hyp, and Gly.

31. The method of claim 29 wherein the added polypeptide comprises at least five contiguous residues of SEQ ID NO: 1.

32. The method of claim 29 wherein the added polypeptide comprises a sequence selected from the group consisting of SEQ ID NO: 1, a variant thereof, and a fragment thereof, wherein the variant includes conservative substitutions of residues other than glycine.

33. The method of claim 32 wherein the added polypeptide is at least about 80% identical to SEQ ID NO: 1.

34. The method of claim 29 wherein the added polypeptide comprises a sequence selected from the group consisting of SEQ ID NO: 3, SEQ ID NO: 5, SEQ ID NO: 7, and fragments thereof.

35. The method of claim 29 wherein the added polypeptide is between about 600-2800 Da.

36. The method of claim 29 wherein the added polypeptide is cationic.

37. The method of claim 29 wherein the composition is a food product.

38. The method of claim 37 wherein the food product is selected from the group consisting of ice cream, dough, frozen desserts, frozen pizza, fruits, and vegetables.

39. The method of claim 29 wherein the polypeptide is added in an amount of at least about 0.1%.

40. The antifreeze composition of claim 29 wherein polypeptide consists entirely of repeating units of the sequence Gly-Z-X.

* * * * *

SEQUENCE LISTING

```
<160> NUMBER OF SEQ ID NOS: 9

<210> SEQ ID NO 1
<211> LENGTH: 21
<212> TYPE: PRT
<213> ORGANISM: Bos primigenius
<220> FEATURE:
<221> NAME/KEY: MOD_RES
<222> LOCATION: (6)..(6)
<223> OTHER INFORMATION: Pro, 3Hyp, or 4Hyp
<220> FEATURE:
<221> NAME/KEY: MOD_RES
<222> LOCATION: (15)..(15)
<223> OTHER INFORMATION: Pro, 3Hyp, or 4Hyp

<400> SEQUENCE: 1

Gly Glu Arg Gly Phe Xaa Gly Glu Arg Gly Val Glu Gly Pro Xaa Gly
1               5                   10                  15

Pro Ala Gly Pro Arg
            20

<210> SEQ ID NO 2
<211> LENGTH: 63
```

```
<212> TYPE: DNA
<213> ORGANISM: Artificial Sequence
<220> FEATURE:
<223> OTHER INFORMATION: Artificial sequence encoding SEQ ID NO: 1

<400> SEQUENCE: 2
ggggaacgcg ggtttcccgg ggaacgcggg gttgaagggc ccccgggcc cgccgggccc    60 cgc                                                                 63

<210> SEQ ID NO 3
<211> LENGTH: 7
<212> TYPE: PRT
<213> ORGANISM: Artificial Sequence
<220> FEATURE:
<223> OTHER INFORMATION: Antifreeze peptide sequence
<220> FEATURE:
<221> NAME/KEY: MOD_RES
<222> LOCATION: (2)..(2)
<223> OTHER INFORMATION: Pro, 3Hyp, or 4Hyp
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Pro, 3Hyp, or 4Hyp
<220> FEATURE:
<221> NAME/KEY: MISC_FEATURE
<222> LOCATION: (6)..(6)
<223> OTHER INFORMATION: Any amino acid

<400> SEQUENCE: 3

Gly Xaa Xaa Gly Xaa Xaa Gly
1               5

<210> SEQ ID NO 4
<211> LENGTH: 21
<212> TYPE: DNA
<213> ORGANISM: Artificial Sequence
<220> FEATURE:
<223> OTHER INFORMATION: Artificial sequence encoding SEQ ID NO: 3
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (16)..(18)
<223> OTHER INFORMATION: n is a, c, g, or t

<400> SEQUENCE: 4
gggcccnnng ggcccnnngg g                                             21

<210> SEQ ID NO 5
<211> LENGTH: 7
<212> TYPE: PRT
<213> ORGANISM: Artificial Sequence
<220> FEATURE:
<223> OTHER INFORMATION: Antifreeze peptide sequence
<220> FEATURE:
<221> NAME/KEY: MOD_RES
<222> LOCATION: (2)..(2)
<223> OTHER INFORMATION: Pro, 3Hyp, or 4Hyp
<220> FEATURE:
<221> NAME/KEY: MOD_RES
<222> LOCATION: (3)..(3)
<223> OTHER INFORMATION: Pro, 3Hyp, or 4Hyp
<220> FEATURE:
<221> NAME/KEY: MOD_RES
<222> LOCATION: (5)..(5)
<223> OTHER INFORMATION: Pro, 3Hyp, or 4Hyp
```

-continued

```
<400> SEQUENCE: 5

Gly Xaa Xaa Gly Xaa Ala Gly
1               5

<210> SEQ ID NO 6
<211> LENGTH: 21
<212> TYPE: DNA
<213> ORGANISM: Artificial Sequence
<220> FEATURE:
<223> OTHER INFORMATION: Artificial sequence encoding SEQ ID NO: 5

<400> SEQUENCE: 6 gggcccccccg ggcccgccgg g                                           21

<210> SEQ ID NO 7
<211> LENGTH: 10
<212> TYPE: PRT
<213> ORGANISM: Artificial Sequence
<220> FEATURE:
<223> OTHER INFORMATION: Antifreeze peptide sequence
<220> FEATURE:
<221> NAME/KEY: MOD_RES
<222> LOCATION: (2)..(2)
<223> OTHER INFORMATION: Pro, 3Hyp, or 4Hyp
<220> FEATURE:
<221> NAME/KEY: MOD_RES
<222> LOCATION: (3)..(3)
<223> OTHER INFORMATION: Pro, 3Hyp, or 4Hyp
<220> FEATURE:
<221> NAME/KEY: MOD_RES
<222> LOCATION: (5)..(5)
<223> OTHER INFORMATION: Pro, 3Hyp, or 4Hyp
<220> FEATURE:
<221> NAME/KEY: MOD_RES
<222> LOCATION: (8)..(8)
<223> OTHER INFORMATION: Pro, 3Hyp, or 4Hyp

<400> SEQUENCE: 7

Gly Xaa Xaa Gly Xaa Ala Gly Xaa Ala Gly
1               5                   10

<210> SEQ ID NO 8
<211> LENGTH: 30
<212> TYPE: DNA
<213> ORGANISM: Artificial Sequence
<220> FEATURE:
<223> OTHER INFORMATION: Artificial sequence encoding SEQ ID NO: 7

<400> SEQUENCE: 8 gggcccccccg ggcccgccgg gcccgccggg                                  30

<210> SEQ ID NO 9
<211> LENGTH: 7
<212> TYPE: PRT
<213> ORGANISM: Artificial Sequence
<220> FEATURE:
<223> OTHER INFORMATION: Antifreeze Peptide
<220> FEATURE:
<221> NAME/KEY: MOD_RES
<222> LOCATION: (2)..(2)
<223> OTHER INFORMATION: Pro, 3Hyp, or 4Hyp
<220> FEATURE:
<221> NAME/KEY: MOD_RES
<222> LOCATION: (5)..(5)
<223> OTHER INFORMATION: Pro, 3Hyp, or 4Hyp

<400> SEQUENCE: 9

Gly Xaa Thr Gly Xaa Leu Gly
1               5
```